(12) United States Patent
Veeningen et al.

(10) Patent No.: US 10,848,311 B2
(45) Date of Patent: Nov. 24, 2020

(54) EDIT SCRIPT VERIFICATION WITH MATCH OPERATIONS AND DIFFERENCE OPERATIONS

(71) Applicant: KONINKLIJKE PHILIPS N.V., Eindhoven (NL)

(72) Inventors: Meilof Geert Veeningen, Eindhoven (NL); Berry Schoenmakers, Eindhoven (NL); Sakina Asadova, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 154 days.

(21) Appl. No.: 16/110,222

(22) Filed: Aug. 23, 2018

(65) Prior Publication Data

US 2019/0068374 A1 Feb. 28, 2019

Related U.S. Application Data

(60) Provisional application No. 62/549,683, filed on Aug. 24, 2017, provisional application No. 62/678,427, filed on May 31, 2018.

(51) Int. Cl.
*G06F 40/00* (2020.01)
*H04L 9/32* (2006.01)
(Continued)

(52) U.S. Cl.
CPC ...... *H04L 9/3218* (2013.01); *G06F 16/90344* (2019.01); *G06F 21/62* (2013.01);
(Continued)

(58) Field of Classification Search
CPC ..... G06F 40/205; G06F 40/226; G06F 40/194
See application file for complete search history.

(56) References Cited

U.S. PATENT DOCUMENTS 7,313,555 B2 12/2007 Klier
2011/0252068 A1* 10/2011 Smith ............... G06F 8/658
707/797
(Continued)

FOREIGN PATENT DOCUMENTS

WO 2008135951 A1 2/2008

OTHER PUBLICATIONS

Atallah, Mikhail J. et al "Secure Outsourcing of Sequence Comparisons", Int. J. Inf. Secur. vol. 4, 2005, pp. 277-287.
(Continued)

*Primary Examiner* — Daniel Abebe

(57) ABSTRACT

Some embodiments are directed to a computation device configured to verify that an edit script is for transforming a first string to a second string. The edit script has match operations and difference operations as allowed edit operations. The computation device obtains a representation of the edit script and subsequently performs a validation computation. For each match operation, the computation device determines a character at a current position in the first string and a character at a current position in the second string, verifies that they match, increments the current position in the first string by one and increments the current position in the second string by one. For each difference operation, the computation device increments the current position in the first string and/or the current position in the second string by one.

18 Claims, 7 Drawing Sheets

(51) Int. Cl.
G06F 21/62 (2013.01)
H04L 9/08 (2006.01)
G06F 40/151 (2020.01)
G06F 40/194 (2020.01)
G06F 16/903 (2019.01)
G16B 30/00 (2019.01)
G16B 50/00 (2019.01)

(52) U.S. Cl.
CPC ........ *G06F 21/6245* (2013.01); *G06F 40/151* (2020.01); *G06F 40/194* (2020.01); *H04L 9/085* (2013.01); *H04L 9/3236* (2013.01); *G16B 30/00* (2019.02); *G16B 50/00* (2019.02); *H04L 2209/38* (2013.01); *H04L 2209/46* (2013.01); *H04L 2209/50* (2013.01)

(56) References Cited

U.S. PATENT DOCUMENTS

| | | | |
|---|---|---|---|
| 2011/0252310 A1* | 10/2011 | Rahaman | G06F 40/14 715/255 |
| 2014/0013205 A1* | 1/2014 | Mikhaiel | G06F 40/14 715/234 |
| 2014/0280344 A1 | 9/2014 | Draghicescu | |
| 2018/0041576 A1* | 2/2018 | Meran | G06F 16/23 |
| 2019/0123928 A1* | 4/2019 | Aston | G06Q 10/107 |

OTHER PUBLICATIONS

Atallah, Mikhail J. et al "Secure and Private Sequence Comparisons", WPES, CERIAS Tech Report 2005-38, 2003.

Damgard, Ivan et al "Multiparty Computation from Somewhat Homomorphic Encryption", Nov. 2011.

De Hoogh, S.J.A. "Design of Large Scale Applications of Secure Multiparty Computation: Secure linear Programming", Eindhoven University of Technology, 2012.

Fiore, Dario et al "Hash First, Argue Later, Adaptive Verifiable Computations on Outsourced Data", Proceedings of ACM CCS, 2016.

Veeningen, Meilof "Pinocchio-based Adaptive zk-SNARKs and Secure/Correct Adaptive Function Evaluation", Progress in Cryptology—AFRICACRYPT 2017—9th International Conference on Cryptology in Africa, Dakar, Senegal, May 24-26, 2017, Proceedings, vol. 10239 of Lecture Notes in Computer Science, pp. 21-39, 2017.

Parno, Bryan et al "Pinocchio: Nearly Practical Verifiable Computation". IEEE Symposium on Security and Privacy, 2013.

Schoenmakers, Berry et al "Trinocchio: Privacy-Preserving Outsourcing by Distributed Verifiable Computation", International Conference on Applied Cryptography and Network Security, pp. 346-366. 2016.

Wahby, Riad S. et al "Efficient RAM and control flow in verifiable outsourced computation", 2015 IEEE Symposium.

Backes, Michael et al "ADSNARK: Nearly Practical and Privacy-Preserving", 2015 IEEE Symposium on Security and Privacy.

Li, Heng et al "Fast and Accurate Short Read Alignment with Burrows-Wheeler Transform", Bioinformatics, vol. 25, No. 14, pp. 1754-1760, 2009.

Troncoso-Pastoriza, Juan Ramon et al "Privacy Preserving Error Resilient DNA Searching through Oblivious Automata", ACM 2007.

BOOST documentation Sequence Algorithms, 2012. http://erikerlandson.github.io/algorithm/libs/algorithm/doc/html/algorithm/Sequence.html.

* cited by examiner

EDIT SCRIPT VERIFICATION WITH MATCH OPERATIONS AND DIFFERENCE OPERATIONS

CROSS-REFERENCE TO RELATED APPLICATIONS

This application claims priority to U.S. provisional application No. 62/549,683, filed Aug. 24, 2017; and 62/678,427, filed on May 31, 2018, the entire disclosures of which are hereby incorporated by reference herein for all purposes.

FIELD OF THE INVENTION

The invention relates a computation device, a verification device, a computation method, and a computer readable medium.

BACKGROUND

Finding differences between two strings, e.g., words, is a common problem in areas like genetics or natural language processing. The differences between two strings are commonly represented as an edit script, also known as an edit path, which is a set of difference operations required to transform one string into the other. Difference operations may be, e.g., replacing a character by another character, inserting a character, or removing a character. The dissimilarity between two strings can be measured by assigning a cost, or weight, to each difference operation in the edit script and defining the so-called edit distance between two strings as the minimal total cost of the operations in an edit script for transforming one of the strings into the other string. For instance, a commonly used edit distance is the Levenshtein distance, which has removal, insertion, and substitution as difference operations and assigns a cost of 1 to each of these types of operations.

Edit distance and edit scripts are used in various settings. For instance, they are used in computational biology. One possible application are devices that sequence DNA samples and measure the similarity of the samples, e.g., to match the samples to the same person or family members. They are also used, e.g., in natural language processing to provide similar corrections to spelling mistakes in entered text. In particular, edit distance and edit scripts are used when searching for a target string in a reference string while allowing for a certain number of mismatches, e.g., to find a substring in the reference string with a small edit distance to the target string. This is used in DNA sequence alignment, where short samples of DNA are matched with a reference genome to find their location. Here, mismatches may occur both because of read errors and because DNA slightly differs from person to person.

There is a need to be able to verify, once an edit script has been determined, that this edit script is indeed for transforming a first string, e.g., a substring of a reference string, to a second string, e.g., a search string. This is the case, for instance, when the worker device determining the edit script is different from the client device that needs to be sure it is correct. For instance, this could be because the client device is resource constrained, e.g., it is a sensor or smart device. It could also be because the client device does not have access to the first string and/or reference string. For example, consider a home DNA sequencing device that obtains and stores genomic data of its user, and an insurance company, acting as the client, wanting to know whether a particular piece of DNA occurs in the genomic data of the user, at least approximately. In such a case, the genomic data may be stored by the user but the insurance company still wants to know that it receives correct answers to its queries about that data.

Unfortunately, verifying that an edit script is for transforming a first string to a second string may leak data about the first and/or second string in several ways, which may be a problem especially if the strings are sensitive, e.g., if they are medical information like genomic data. For instance, other applications running on the device verifying the edit script may be able to observe information about the memory access pattern of the verification and try to use this information to derive information about the data being verified. Also, in settings where (parts of) the first and/or second string and/or the edit script come from multiple mutually distrusting parties, verifying would require these parties to share their inputs to whomever needs to check that the edit script is correct. Similarly, in settings where a client device needs to verify correctness of an edit script determined by a working device, verifying would require the client to inspect inputs like the first string, the second string, or the edit script. This may be undesirable from a privacy point of view, for example, in the home DNA sequencing application it would mean letting the insurance company inspect the genomic data of its users. It may also simply be undesirable because of resource limitations for the client device to perform a verification procedure using this data since such a computation scales in the size of its inputs, e.g. the first or second string, or the edit string.

SUMMARY OF THE INVENTION

A computation device as defined in the claims is proposed. The computation device is for verifying that an edit script is for transforming a first string to a second string. The computation device provides data-obliviousness advantages. Data-obliviousness means that an access pattern, e.g., the pattern of accessed memory locations or files retrieved from remote storage, is equivalent for different inputs. When verifying an edit script, this means, e.g., that the access pattern is equivalent for different edit scripts that have the same length but contain different difference operations. Thereby the amount of information is reduced that may leak about the first string and/or edit string and/or edit script when performing the verification, for instance, via side-channels. The computation device is configured to obtain a representation of the edit script and subsequently perform a validation computation to verify that it is correct.

Interestingly, in addition to the normal difference operations, the set of allowed edit operations of the edit script additionally comprises match operations. Adding this match operation has the advantage that it enables the verification to be performed in a more data-oblivious way, since the verification can be performed by iterating through the first string, second string and edit string in a linear fashion, giving similar access pattern for different edit strings. Having obtained such an edit script, the computation device can perform a validation computation to obtain assurance of the correctness of the edit script wherein, for each match or difference operation in the edits script, the current position in the first string and/or the current position in the second string is incremented by one. In particular, many edit scripts will produce similar access patterns. In particular, a character at a current position in the first or second string may be computed as an inner product between a binary vector and one or more characters of the first or second string so that determining said character involves accessing multiple characters of the first or second string, further improving data-obliviousness since the current character be directly observed from observing which character is accessed.

In an embodiment, computation devices are used in a multiparty computation system. By performing the validation computation using multi-party computation (MPC), multiple mutually distrusting parties can gain assurance of the correctness of the edit script without the need to share their sensitive inputs, e.g., the first string, second string, or edit script. The data-obliviousness improvements of our computation device are particularly advantageous in this setting since they allow the sensitive intermediate results of the validation computation, that indirectly leak information about the inputs, to remain hidden from the computation devices. In an embodiment, a first computation device provides the first string as a private input to the multi-party computation and a second computation device provides the second string as a private input to the multi-party computation. Here, the data-obliviousness characteristics of the computation devices help to reduce the amount of information derivable about the first string by computation devices other than the second computation device and about the second string by computation devices other than the first computation device. In an embodiment, a first computation device provides the second string as a private input to the multi-party computation, the first string being a public input to the multi-party computation. Here, the data-obliviousness characteristics of the computation devices help to reduce the amount of information derivable about the second string by computation devices other than the first computation device.

In an embodiment, the computation device is configured with a maximum edit distance, e.g., comprising the Levenshtein distance, between the first string and the second string. The set of allowed edit operations may comprise dummy operations, and the number of edit operations that the edit script comprises may be a function of the length of the first string, the length of the second string, and the maximum edit distance. Hence, potential leakage of sensitive information, e.g., about the first or second string, is further reduced by making sure that many different first strings or different second strings can have edit scripts of the same length. In some embodiments, such an edit script is generated by identifying allowable edit operations from the first string and second string and adding said allowable edit operations to the edit script, a dummy operation being added to the edit script if a mismatch operation or insertion operation is added to the edit script. Hence the dependence of the length of intermediate copies of the edit script on the contents of the first and second string is reduced, also improving the data-obliviousness characteristics of edit script generation.

A further aspect of the invention is a verification device. In an embodiment, a computation device and a verification device are used in a verifiable computation system. In such a system, the computation device performs the validation computation as a verifiable computation generating a cryptographic verifiable computation proof that the validation computation was performed successfully and provides the cryptographic proof to the verification device so that the verification device obtains assurance of the correctness of the edit script. The verification device receives and verifies the proof. This enables the verification device to outsource the computation to the computation device while still obtaining assurance that was correctly performed. The data-obliviousness characteristics of the verification allow the same proof generation and verification procedures to be applicable to computations on different inputs, and in particular, the verification device may perform the same verification procedure regardless of the size of the inputs. The data-obliviousness characteristics of the verification also enable the possibility to keep some or all of the processed information hidden from the verification device. In particular, in some embodiments, the verification device receives an input representation by a data providing device of the first string, of a larger string of which the first string is a substring, or of the root of a Merkle hash tree of which the larger string is a data block, wherein data-obliviousness enables the first and/or second string to remain hidden from the verification device while the verification device still receives some guarantee of its authenticity.

A further aspect of the invention is a computation method. An embodiment of the method may be implemented on a computer as a computer implemented method, or in dedicated hardware, or in a combination of both. Executable code for an embodiment of the method may be stored on a computer program product. Examples of computer program products include memory devices, optical storage devices, integrated circuits, servers, online software, etc. Preferably, the computer program product comprises non-transitory program code stored on a computer readable medium for performing an embodiment of the method when said program product is executed on a computer.

In an embodiment, the computer program comprises computer program code adapted to perform all the steps of an embodiment of the method when the computer program is run on a computer. Preferably, the computer program is embodied on a computer readable medium.

Another aspect of the invention provides a method of making the computer program available for downloading. This aspect is used when the computer program is uploaded into, e.g., Apple's App Store, Google's Play Store, or Microsoft's Windows Store, and when the computer program is available for downloading from such a store.

BRIEF DESCRIPTION OF THE DRAWINGS

Further details, aspects, and embodiments of the invention will be described, by way of example only, with reference to the drawings. Elements in the figures are illustrated for simplicity and clarity and have not necessarily been drawn to scale. In the figures, elements which correspond to elements already described may have the same reference numerals. In the drawings, FIG. 1a schematically shows an example of an embodiment of a computation device, FIG. 1b schematically shows an example of an embodiment of a computation device, FIG. 2 schematically shows an example of an embodiment of a computation device, FIG. 3 schematically shows an example an embodiment of a character matching unit, FIG. 4a schematically shows an example of an embodiment of a multiparty computation system, FIG. 4b schematically shows an example of an embodiment of a multiparty computation system FIG. 4c schematically shows an example of an embodiment of a multiparty computation system, FIG. 4d schematically shows an example of an embodiment of a multiparty computation system, FIG. 5a schematically shows an example of an embodiment of a verifiable computation system, FIG. 5b schematically shows an example of an embodiment of a verifiable computation system, FIG. 5c schematically shows an example of an embodiment of a verifiable computation system, FIG. 6 schematically shows an example of an embodiment of a computation method, FIG. 7a schematically shows a computer readable medium having a writable part comprising a computer program according to an embodiment, FIG. 7b schematically shows a representation of a processor system according to an embodiment.

LIST OF REFERENCE NUMERALS IN FIGS. 1a, 1b, 2, 3, 4a-4d, 5a-5c, 7a, 7b 110,111 a computation device
120 a communication interface
121 a computer network
130 a memory
131 an edit script representation
131.1, 131.2 an edit operation
132 a representation of a current position in the first string
133 a representation of a current position in the second string
134 a first string
134.1, 134.2 a character of the first string
135 a second string
135.1, 135.2 a character of the second string
136 a larger string
137 a Merkle hash tree
140 a processor
141 an edit script obtainer unit
142 a validation unit
143 a first position incrementing unit
144 a second position incrementing unit
145 a character matching unit
150 a first binary vector
150.1, 150.2 an element of the first binary vector
151 the character at the current position in the first string
160 a second binary vector
160.1, 160.2 an element of the second binary vector
161 the character at the current position in the second string
400,401 a multiparty computation system
500 a verifiable computation system
510 a verification device
511 a data providing device
520 a communication interface
521 a computer network
522 a cryptographic verifiable computation proof
523 an input representation
530 a memory
540 a processor
1000 a computer readable medium
1010 a writable part
1020 a computer program
1110 integrated circuit(s)
1120 a processing unit
1122 a memory
1124 a dedicated integrated circuit
1126 a communication element
1130 an interconnect
1140 a processor system

DETAILED DESCRIPTION OF THE EMBODIMENTS

Figure 1A:
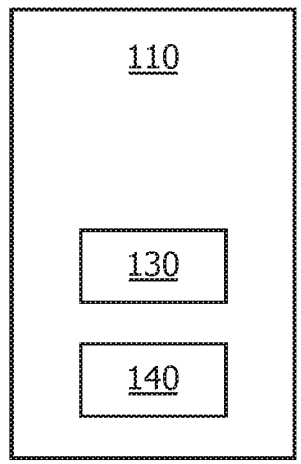

While this invention is susceptible of embodiment in many different forms, there are shown in the drawings and will herein be described in detail one or more specific embodiments, with the understanding that the present disclosure is to be considered as exemplary of the principles of the invention and not intended to limit the invention to the specific embodiments shown and described.

In the following, for the sake of understanding, elements of embodiments are described in operation. However, it will be apparent that the respective elements are arranged to perform the functions being described as performed by them.

Further, the invention is not limited to the embodiments, and the invention lies in each and every novel feature or combination of features described herein or recited in mutually different dependent claims.

Some of the embodiments presented below provide data-obliviousness advantages for a computation device configured to verify that an edit script is for transforming a first string to a second string. When a device performs a computation, various kinds of information may leak about the data that is being computed on through side channels. For instance, as the recent Spectre and Meltdown attacks on computer processors using speculative execution have demonstrated, a computer program may be able to extract sensitive data from another computer program running on the same computation device through a cache timing side channel. In order to thwart such attacks, it is advantageous if the memory access pattern of computations executed by a processor can be made less dependent on any sensitive data that the computation processes. For instance, it is advantageous for a computation device to be designed in such a way that the memory access pattern of the processor only depends on the size of some or all of the processed information, and not on its contents.

Some embodiments focus improving data-obliviousness in the case when the edit script is valid. If the edit script is not for transforming a first string to a second string, e.g., it is invalid, data-obliviousness may be less of a concern, e.g., it may not be needed to protect which operation from the edit script was invalid or which characters from the first or second string caused the edit script to be invalid. For instance, in some embodiments, the device that needs to protect the first string and/or the second string and/or the edit script has itself generated the edit script and is therefore sure that the edit script is valid; it may perform the verification only to convince others of its correctness. This makes it irrelevant what happens if the edit script is invalid. In some embodiments, if the edit script is invalid, the edit script verification procedure is terminated, or a flag is set indicating the error and the edit script verification procedure proceeds, e.g., verification continues to the end of the edit script even if there is an error.

Some embodiments presented below provide data-obliviousness advantages for a computation device configured to verify that an edit script is for transforming a first string to a second string using multi-party computation (MPC). In multi-party computation, multiple computation devices may perform a distributed computation on their respective inputs in such a way that a computation device does not learn some or all of the inputs of other computation devices. Various techniques for performing MPC known to the person skilled in the art can be used in embodiments below, as discussed in more detail later. A common characteristic of many MPC techniques, though, is that the control flow, e.g., memory access patterns or conditional branches, of the computation performed with MPC should not depend on the contents of sensitive data, e.g., a sensitive input by a computation device or data that has been computed based on sensitive inputs. Hence, in order to hide sensitive data in a MPC, it is advantageous to reduce the dependence of the control flow on the contents of sensitive data, e.g., to improve the data-obliviousness of the computation performed in the MPC. For instance, it is advantageous to design the computation device in such a way that the memory access pattern of the program depends on the size of some or all of the processed information, but less on its contents.

Some embodiments presented below provide data-obliviousness advantages for a computation device configured to verify that an edit script is for transforming a first string to a second string as a verifiable computation generating a cryptographic verifiable computation proof, and for a verification device configured to verify that an edit script is for transforming a first string to a second string by verifying said cryptographic verifiable computation proof. In verifiable computation, the proof provides to the verifier cryptographic guarantees about the correctness of the edit script without the verifier needing to perform the verification by itself. This may, e.g., save computational effort or storage capacity required by the verifier. In verifiable computation, some or all of key material needed by the computation device, key material needed by the verification device, or the verification procedure performed by the computation device may depend on the control flow, e.g., memory access patterns or conditional branches, of the computation performed as a verifiable computation. Hence, in order to eliminate the need for different key material and/or different verification procedures, it is advantageous to reduce the dependence of the control flow on the input data, e.g., to improve the data-obliviousness of the computation. In some embodiments, the cryptographic proof is a zero-knowledge proof that hides some or all of the data used in the verification, e.g., the verifiable computation may employ a zero-knowledge succinct non-interactive argument of knowledge (zk-SNARK). This may enable the verifier to get assurance about the correctness of the edit script without necessarily needing to know the first string and/or the second string and/or the edit script. In such cases, also from a privacy point of view, it is advantageous to reduce the dependence of the control flow on these sensitive inputs.

FIG. 1a schematically shows an embodiment of a computation device 110. FIG. 1a shows computation device 110 comprising a memory 130 and a processor 140. Memory 130 may be used for data and/or instruction storage. For example, memory 130 may comprise software and/or data on which processor 140 is configured to act. Processor 140 may be implemented as one or more processor circuits, e.g. microprocessors, ASICs, FPGA and the like. Memory 130 may comprise computer program instructions which are executable by processor 140. Processor 140, possibly together with memory 130, is configured according to an embodiment of a computation device.

Figure 1B:
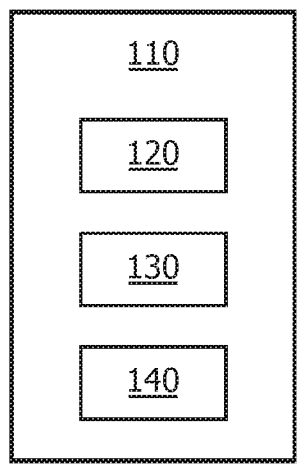

FIG. 1b schematically shows an embodiment of computation device 110. FIG. 1b shows a computation device 110 comprising a communication interface 120 configured for digital communication with one or more other computation devices, a memory 130, and a processor 140.

Figure 2:
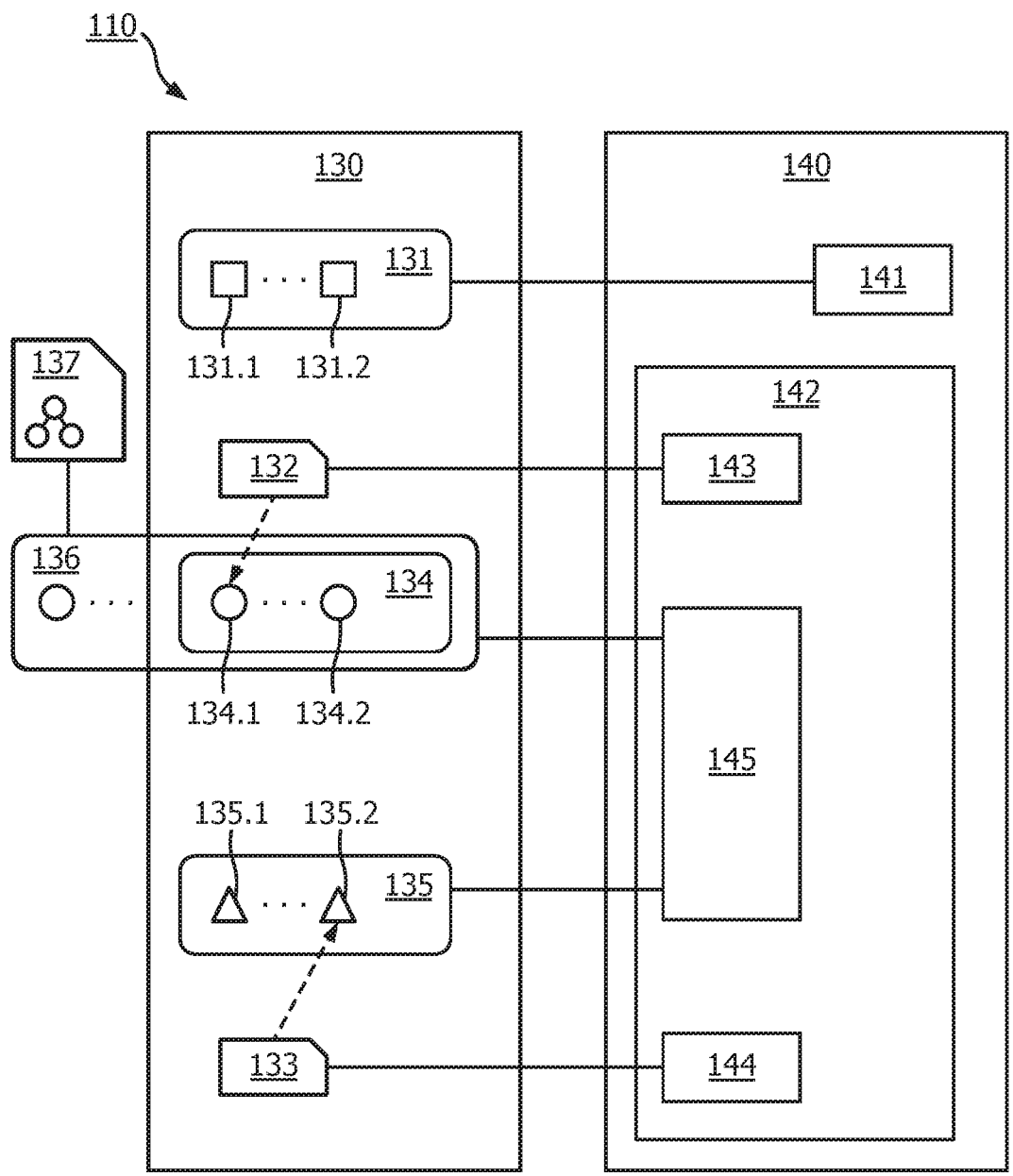

The execution of computation device 110 is implemented in processor 140. For example, processor 140 may be a microprocessor, FPGA, ASIC, or combination thereof. Processor 140 may be provisioned, e.g., within a cloud computing architecture, etc. Further examples are shown herein. FIG. 2 schematically shows functional units that may be functional units of processor 140. For example, FIG. 2 may be used as a blueprint of a possible functional organization of processor 140. For example, the functional units shown in FIG. 2, e.g., the validation unit 142, may be wholly or partially be implemented in computer instructions that are stored at device 110, e.g., in an electronic memory of device 110, and are executable by a microprocessor of device 110. In hybrid embodiments, functional units are implemented partially in hardware, e.g., as coprocessors, and partially in software stored and executed on device 110.

Computation device 110 is configured to verify that an edit script 131 is for transforming a first string 134 to a second string 135. An edit script 131 comprises one or more edit operations, e.g., edit operations 131.1, 131.2, the edit operations being selected from a set of allowed edit operations. If edit script 131 is for transforming first string 134 to second string 135, then applying the operations from edit script 131 to first string 134 results in second string 135. We refer to edit script 131 as "valid" in this case, otherwise as "invalid". The set of allowed edit operations includes difference operations indicating a difference between first string 134 and second string 135. Examples of difference operations include mismatch operations, wherein a character from first string 134 is replaced by another character to obtain second string 135, insertion operations, wherein a character is inserted into first string 134 to obtain second string 135, and deletion operations, wherein a character is deleted from first string 134 to obtain second string 135. A particular computation device 110 may support any subset of these difference operations, e.g., computation device 110 may just support mismatches or computation device 110 may just support mismatches and deletions; and computation device 110 may support operations beyond those mentioned above, e.g., transposition operations, merging operations, or splitting operations.

Memory 130 is configured to store a representation of one or more characters, e.g., characters 134.1, 134.2, of first string 134 and one or more characters, e.g., characters 135.1, 135.2, of second string 135. Various ways of representing a character are possible, e.g., using ASCII, or by assigning each character a number in a finite field, e.g., 'A'=0, 'B'=1, etc., or as encryptions or secret-shares as discussed in detail for particular embodiments below. Representations of all characters of first string 134 and second string 135 may be stored in the memory, but this is not necessary; for instance, if first string 134 is very large it is not necessary to have the whole first string in the memory all the time but instead computation device 110 may have different parts of first string 134 in memory 130 at different stages in the verification; similarly, it is not necessary to have the whole second string 135 in memory 130 all the time but instead computation device 110 may have different parts of second string 135 in memory 130 at different stages in the verification. Memory 130 is additionally configured to store a representation 132 of a current position in the first string 134 and a representation 133 of a current position in the second string 135. Initially, positions 132 and 133 may point to the start of the first and second string, respectively. Various ways of representing such positions are possible, e.g., as bytes, integers, field elements, secret shares, or encryptions. In some embodiments, first string 134 and second string 135 are nucleic acid sequences, e.g., DNA or RNA sequences comprising characters 'A', 'C', G', and 'T'. In this case, due to the sensitivity of the data involved, there is a particular need for data-oblivious verification techniques. Efficient ways of representing nucleic acid sequences in memory, e.g., by packing four characters in a single byte or by performing compression, are known in the state of the art.

Processor 140 comprises an edit script obtainer unit 141 configured to obtain a representation of the edit script and store it in memory 130.

Conventionally, an edit script only comprises difference operations. For instance, an edit script may comprise the three difference operations "replace A by C at 2", "insert C at 5", and "delete at 8". This edit script transforms first string s="AACTGCTAT" to second string t=" ACCTCGCAT", as can be verified by applying the subsequent difference operations of the edit script. For instance, applying difference operation "replace A by C at 2" to s gives s'="ACCTGCTAT"; applying difference operation "insert C at 5" to s' gives s"="ACCTCGCTAT", and applying difference operation "delete at 8" to s" gives t="ACCTCGCAT". Hence this edit script is valid for transforming s to t. Although applying subsequent difference operations allows verifying that an edit script is valid, it is not obvious how this can be performed in a data-oblivious way, e.g., the memory access pattern for applying a deletion operation may be different from the memory access pattern for an insertion operation, and the memory access pattern for an insertion at location 1 may be different from the memory access pattern for an insertion at location 5.

Interestingly however, the set of allowed edit operations for edit script 131 contains not just difference operations but also match operations indicating that the same character occurs both in first string 134 and in second string 135. For instance, edit script 131 may be represented as a sequence of edit operations, e.g., edit operations 131.1, 131.2, including match operations in such a way that, for each character in first string 134 that is not addressed by a difference operation, e.g., replaced or deleted, a match operation is included. For instance, the above edit script [replace A by C at 2, insert C at 5, delete at 8] may be represented as the following sequence of edit operations including match operations: [match; mismatch A/C; match; match; insert C; match; match; delete T; match; match]. Here, match operations are included for the first, third, fourth, fifth, sixth, eighth and ninth character of the first string since these characters are not replaced or deleted in order to obtain the second string from the first string. Adding these match operations improves the data-obliviousness of verifying that edit script 131 is valid since it allows edit script 131 to be verified, for instance, by, for each operation, e.g., operations 131.1, 131.2, in the edit script, incrementing representation 132 of the current position in the first string and/or representation 133 of the current position in the second string by one if the operation is a match operation or a difference operation, and, as a consequence, edit script verifications for different first strings 134 and/or second strings 135 and/or edit scripts 131 may have similar access patterns to memory 130.

In some embodiments, computation device 110 may obtain just the type for each edit operation, e.g., whether the edit operation represents a match operation, a mismatch operation, an insertion operation, or a deletion operation. For example, each operation may be represented by a code. The code may identify the particular type of operation. In other embodiments, additional information about each edit operation, e.g., edit operation 131.1 or 131.2, may be obtained, such as the location at which it occurs or the particular character that is inserted or deleted. As above, the information obtained about each edit operation, e.g., edit operation 131.1 or 131.2, may be represented in various ways, e.g., in ASCII, as one or more field elements, as a share in a secret sharing or as an encryption.

Edit script 131 may be obtained in various ways. For instance, edit script 131 may be computed by computation device 110 itself, in which case edit script 131 may be obtained via an intra-device communication interface, a function call, an API, a bus, etc. Alternatively, computation device 110 may comprise a communication interface 121 configured for digital communication with a further communication device 111 and computation device 110 may receive the representation of edit script 131 via the communication interface. Computation device 110 may or may not have contributed towards computing edit script 131. For instance, another device may compute edit script 131 and provide it to computation device 110, in which case edit script 131 may be represented in the plain. Alternatively, edit script 131 may be the result of a multiparty computation between the computation device 110 and other computation devices, e.g., computation device 111, in which case edit script 131 may be represented as secret shares or encryptions, or edit script 131 may be the result of a multiparty computation by another group of computation devices, in which case edit script 131 may also be represented as secret shares or encryptions.

Processor 140 further comprises a validation unit 142 that, subsequently to edit script obtainer unit 141 obtaining and storing edit script 131, performs a validation computation. Validation unit 142 itself comprises several units that perform particular actions involving strings 134, 135 and representations 132, 133 of the current positions in the respective strings. In particular, validation unit 142 comprises a first position incrementing unit 143, a second position incrementing unit 144, and a character matching unit 145. In some embodiments, validation unit 142 activates units 143, 144, and 145 depending on the type of each edit operation in edit script 131, for instance, validation unit 142 may iterate through operations, e.g., operation 131.1 or 131.2, of edit script 131 sequentially and call units 143, 144, and 145 depending on the type of edit operation. In other embodiments, validation unit 142 calls units 143, 144, 145 for each edit operation, e.g., validation unit 142 may iterate through edit script 131 sequentially and call each unit 143, 144, and 145 for each edit operation. In such other embodiments, units 143, 144, 145 may be configured to perform dummy operations in case the current edit operation does not require them to change the memory, which may be beneficial for data-obliviousness. For example, unit 142 may determine a flag denoting whether or not the current edit operation requires any one of units 143, 144 or 145 to change the memory 130, and any one of units 143, 144 and 145 may perform their operations by updating one or more values in memory 130 based on the flag, the original value, and the new value if the current edit operation requires the unit to change the memory, for example, by computing the updated value as the sum of the original value and the product of the flag and the difference between the new value and the original value.

First position incrementing unit 143 updates representation 132 of a current position in the first string based on an edit operation, e.g., edit operation 131.1, 131.2, in edit script 131. First position incrementing unit 143 increments the current position 132 in the first string by one for some types of edit operation: for match operations, but possibly also for some kinds of difference operations, e.g., for mismatch operations or deletion operations. First position incrementing unit 143 may be activated only for edit operations that require updating the current position in the first string. Alternatively, it may be activated also for other edit operations, which may improve data-obliviousness since it reduces the amount of information that can be obtained from observing whether current position 132 is updated. For instance, it may be activated for all edit operations, e.g., edit operations 131.1, 131.2 in edit script 131, and update the current position in the first string 132 by setting it to xpos+ismatch+ismismatch+isdeletion, where xpos is the current position in the first string, ismatch is 1 if the edit operation is a match operation and 0 otherwise, ismismatch is 1 if the edit operation is a mismatch operation and 0 otherwise, and isdeletion is 1 if the edit operation is a deletion operation and 0 otherwise. In some embodiments, the current position in the first string 132 is updated as a multi-party computation, wherein ismatch, ismismatch, and isdeletion may be computed data-obliviously using known techniques, e.g., a comparison protocol, as elaborated in more detail below. In some embodiments, current position in the first string 132 is updated as a verifiable computation, wherein ismatch, ismismatch, and isdeletion may be computed data-obliviously using known techniques, e.g., using a zero-equality gate, as elaborated in more detail below.

Second position incrementing unit 144 updates representation 133 of a current position in the second string based on an edit operation, e.g., edit operation 131.1, 131.2 in edit script 131. Second position incrementing unit 144 increments current position 133 in the second string by one for some types of edit operation: for match operations, but possibly also for some kinds of difference operations, e.g., for mismatch operations or insertion operations. Second position incrementing unit 144 may be activated only for edit operations that require updating the current position in the first string. Alternatively, it may be activated also for other edit operations, which may improve data-obliviousness since it reduces the amount of information that can be obtained from observing whether current position 133 is updated. For instance, it may be activated for all edit operations, e.g., edit operations 131.1, 131.2 in the edit script 131, and update the current position in the second string 133 by setting it to wpos+ismatch+ismismatch+isinsertion, where wpos is the current position in the second string, ismatch is 1 if the edit operation is a match operation and 0 otherwise, ismismatch is 1 if the edit operation is a mismatch operation and 0 otherwise, and isinsertion is 1 if the edit operation is an insertion operation and 0 otherwise. In some embodiments, current position in the second string 133 is updated as a multi-party computation, wherein ismatch, ismismatch, and isinsertion may be computed data-obliviously using known techniques, e.g., a comparison protocol, as elaborated in more detail below. In some embodiments, current position in the first string 133 is updated as a verifiable computation, wherein ismatch, ismismatch, and isinsertion may be computed data-obliviously using known techniques, e.g., using a zero-quality gate, as elaborated in more detail below.

In an embodiment, first position incrementing unit 143 and second position incrementing unit 144 together do the following for an edit operation, e.g., edit operation 131.1 or 131.2:

if the edit operation is a match operation, current position 132 in the first string is incremented by one by first position incrementing unit 143 and current position 133 in the second string is incremented by one by second position incrementing unit 144, if the edit operation is a difference operation, current position 132 in the first string is incremented by one by first position incrementing unit 143 and/or current position 133 in the second string is incremented by one by second position incrementing unit 144, for example:

if the edit operation is a mismatch operation, current position 132 in the first string is incremented by one by first position incrementing unit 143 and current position 133 in the second string is incremented by one by second position incrementing unit 144, if the edit operation is an insertion operation, current position 133 in the second string is incremented by one by second position incrementing unit 144, and if the edit operation is a deletion operation, current position 132 in the first string is incremented by one by first position incrementing unit 143.

In particular, current position 132 in the first string and current position 133 in the second string may be incremented by either zero or one for each individual edit operation, which may reduce the dependence of the memory access pattern on the contents of edit script 131, thereby improving data-obliviousness.

Character matching unit 145, when activated for a match operation, determines character x at the current position in the first string and the character w at the current position in the second string and verifies that they match, e.g., are equal. If the characters do not match, this gives an indication that edit script 131 is not for transforming first string 134 to second string 135. Character matching unit 145 may be activated not just for match operations but also for other edit operations. For instance, it may be activated for all edit operations, e.g., edit operations 131.1, 131.2. In such cases, an error criterion may be derived from a value indicating whether the current edit operation is a match operation and a value indicating whether the characters match. For instance, a value match may be determined which is 1 if the edit operation is a match and 0 otherwise; and to obtain the error criterion, match may be multiplied with a Boolean value denoted $(x-w\neq 0)$, which is 0 if characters x and w match, e.g., are equal, and 1 otherwise. If the error criterion is 1, this indicates that the edit script is not for transforming first string 134 to second string 135. In this case, e.g., the edit script verification procedure may be terminated, or a flag indicating the error may be set and the edit script verification procedure may proceed.

In some embodiments, at some point during edit script verification, the representation of the current position 132 in the first string and/or the representation of the current position 133 in the second string may be out-of-bounds. For example, representation 132 and/or representation 133 may point to a position outside of the respective strings 134, 135. Note that this does not necessarily imply that edit script 131 is invalid: for instance, if current position 133 in the second string points to the position directly after second string 135 but the remainder of the edit script only contains deletion operations, edit script 131 may still be valid. In such embodiments, it may be beneficial from a data-obliviousness point of view for character matching unit 145 to derive a current character x and/or a current character w even if representation 132 and/or representation 133 is out-of-bounds. For example, character matching unit 145 may be configured to set character x to a special value, say, A, in case representation 132 points to a position directly after first string 134; and/or to set character w to a special value, say, B, in case representation 133 points to a position directly after second string 135. In such cases, character matching unit 145 may derive an error criterion that also takes into account the possibility that position 132 and/or position 133 is out-of-bounds. For instance, the error criterion may be equal to match*$((x=A)+(w=B)+(x-w\neq 0))$+mismatch*$((x=A)+(w=B))$, where match is 1 if the edit operation is a match operation and 0 otherwise; $(x=A)$ is 1 if x is equal to special value A and 0 otherwise; $(w=B)$ is 1 if w is equal to special value B and 0 otherwise; $(x-w\neq 0)$ is 0 if x and w are not equal and 1 otherwise; and mismatch is 1 if the edit operation is a mismatch operation and 0 otherwise. In particular, the error criterion is satisfied, among other cases, if the edit operation is a match or a mismatch but either x or w is equal to its respective special value A or B.

In some embodiments, if representation 132 and/or representation 133 points to a position that is neither inside nor directly after the respective string 134, 135, this may imply that edit script 131 is invalid. In this case, character matching unit 145 may be configured to terminate or set an error flag. In particular, character matching unit 145 may be configured to check, for each edit operation, whether current position 132 is exactly two positions after the end of first string 134 or current position 133 is exactly two positions after the end of second string 135. In some embodiments, current positions 132 and 133 are initially inside the respective strings 134, 135 and are only modified by incrementing them by one, in which case this check may be sufficient.

In some embodiments, validation unit 142 takes additional steps to ensure that the edit script is valid. For instance, validation unit 142 may verify that, after the steps of the validation computation for each edit operation in edit script 131 have been performed, representation 132 of the current position in the first string points exactly to the first character after the end of the first string 134, indicating that the validation computation has verified all characters of first string 134. Similarly, validation unit 142 may verify that, after the steps of the validation computation for each edit operation in edit script 131 have been performed, representation 133 of the current position in the second string points exactly to the first character after the end of the second string 135.

In some embodiments, computation device 110 is configured with a maximum edit distance between first string 134 and second string 135. In some embodiments, the edit distance comprises the Levenshtein distance, defined as the edit distance where the difference operations supported are mismatch operations, deletion operations, and insertion operations, and the cost of each difference operation is one, e.g., the edit distance may be the minimum number of mismatch operations, deletion operations, and insertions operations needed to transform first string 134 to second string 135. The Levenshtein distance is of particular interest due to its widespread use, e.g., in genetics. However, other edit distances are also possible, e.g., insertions operations may have weight two, deletion operations may have weight three, and mismatches may have weight four. It is also possible, for example, for the set of allowed edit operations to only comprise mismatch operations and the cost of these operations to be one, e.g., the edit distance may comprise the Hamming distance or signal distance as used in areas like telecommunication. Or, the set of allowed edit operations may only comprise transposition operations and the cost of these operations may be one, e.g. the edit distance may be the Jaro distance or Jaro-Winkler distance, as used in areas like record linkage. The costs for each type of edit operation are typically predetermined.

In order to improve the data-obliviousness of the edit script verification, the number of edit operations that edit script 131 comprises may be a function of the length of the first string, the length of the second string, and the maximum edit distance. In particular, this number may be independent from the particular contents of first string 134 and second string 135, and of the particular edit operations in edit script 131. Preferably, the number should be such that for all first strings 134 and second strings 135 with the given length that have edit distance at most the given maximum, there is an edit script 131 with length at most this number. For instance, the edit distance may be Levenshtein distance and the length of edit script 131 may be equal to the length of second string 135 plus the maximum edit distance. To ensure that an edit script 131 with exactly this length exists, it is beneficial for the set of allowed edit operations to comprise dummy operations. For instance, first string "AAA" may be transformed to second string "AAB" with Levenshtein distance at most two via a set of edit operations [match, match, mismatch, dummy, dummy] with length equal to the length of the second string plus the maximal edit distance.

In some embodiments, validation unit 142 verifies that the edit distance between first string 134 and second string 135 does not exceed the maximum edit distance. For example, validation unit 142 may keep a running total nerrors of errors encountered so far and update this value for each edit operation that is verified. For instance, the edit distance may be Levenshtein distance and validation unit 142 may set the new value for nerrors to be nerrors+ismismatch+isinsertion+isdeletion, where nerrors is the previous running total, and ismismatch, isinsertion, and isdeletion indicate whether the current edit operation is a mismatch operation, insertion operation or deletion operation, respectively. Validation unit 142 may terminate or set an error flag as soon as the running total exceeds the maximum edit distance; for instance, it may terminate or set an error flag as soon as the running total equals the maximum edit distance plus one.

In some embodiments, the first string 134 may be a substring of a larger string 136. For instance, this may allow verification in the setting where the first string 134 represents a search result in the larger string 136. In such cases, the current position 132 in first string 134 may be expressed as a current position in larger string 136. For instance, first string 134 may start at position 11 in larger string 136, and the position of the second character in first string 134 may be expressed as position 12 in larger string 136. Successful verification that an edit script 131 is for transforming first string 134 to second string 135 in this case indicates that the second string 135 occurs in the larger string 136 with a certain maximum edit distance.

In further applications, the larger string 136 may in turn be a substring of an even larger string, for instance, a DNA sequence capturing the entire genome of a human. In some embodiments, the validation computation further comprises verifying that the larger string 136 occurs as a data block in a Merkle hash tree 137 representing the even larger string. This may be beneficial especially if the even larger string is particularly large considering that the validation computation may scale in the size of the larger string, especially in a data-oblivious setting. As an example, Merkle hash tree 137 may be a binary tree in which the leaf nodes are data blocks and each internal node is the cryptographic hash of the concatenation of its two child nodes. Verifying that the larger string 136 occurs as a data block in Merkle hash tree 137 may comprise obtaining a representation of the root of the Merkle hash tree 137 and representations of all siblings on the path in Merkle hash tree 137 from the data block to the root, recomputing all internal nodes on the path, finally recomputing the root, and verifying that the result equals the obtained root. Merkle hash tree 137 does not need to be a binary tree, e.g., each internal node may correspond to the hash of any number of child nodes, possibly with additional information included.

Figure 3:
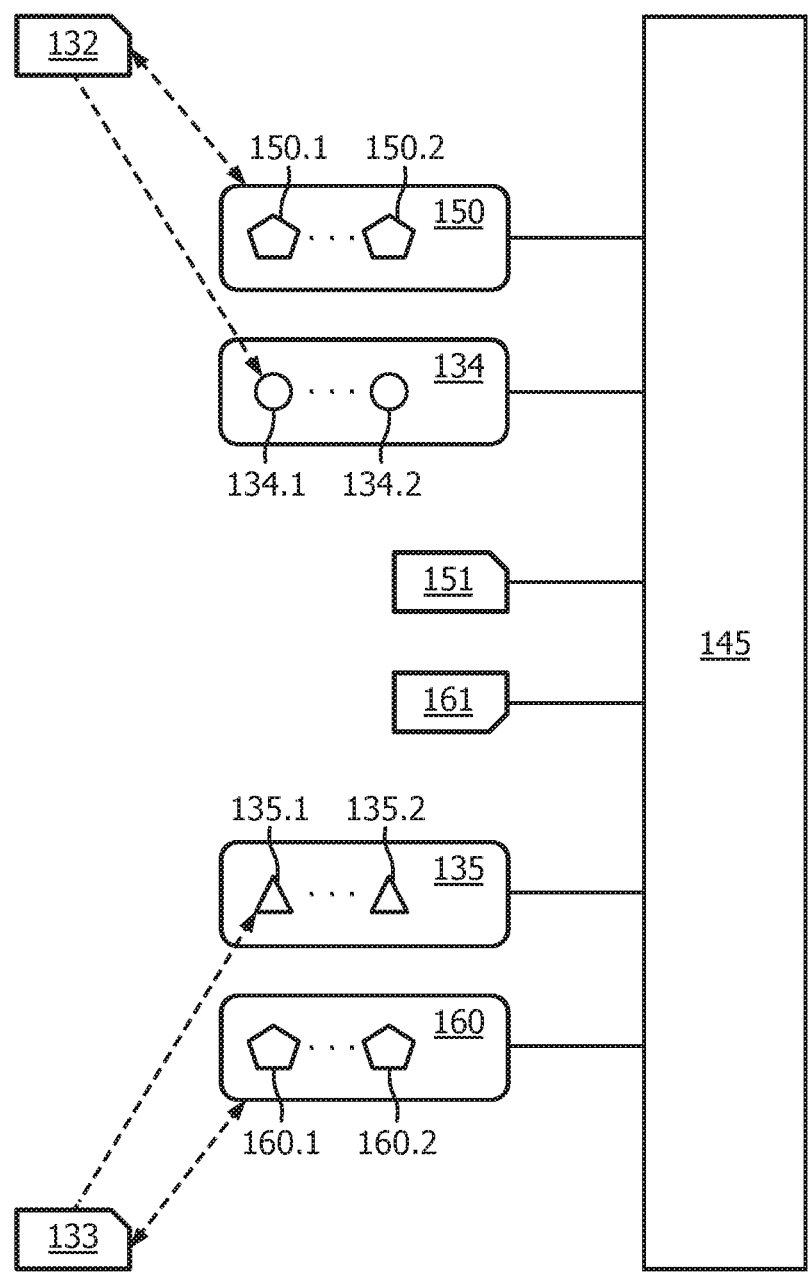

FIG. 3 schematically shows an example an embodiment of a method of matching characters. In order to determine the character 151 (C) at the current position 132 in the first string, character matching unit 145 computes an inner product (C=$\langle \vec{\delta}, \vec{c} \rangle$=$\delta_1 c_1$+ . . . +$\delta_n c_n$), between one or more characters ($\vec{c}=(c_1, \ldots, c_n)$), e.g., characters 134.1, 134.2, of the first string 134, and a first binary vector 150 ($\vec{\delta}=(\delta_1, \ldots, \delta_n)$) indicating which of the one or more characters is the character at current position 132 in the first string, e.g., $\delta_i$ is 1 if $c_i$ is the current character and 0 otherwise. The first binary vector typically comprises at most one 1. Since the inner product computation may access other characters in addition to the character at the current position 132 in the first string, using an inner product may reduce the dependence of the memory access pattern on the particular current position 132, hence improving data-obliviousness. The inner product may an inner product between all characters of the first string 134 and bits, e.g., bits 150.1, 150.2, of a correspondingly large binary vector 150, but this is not necessarily the case. For instance, the inner product may be an inner product between a subset of the characters of the first string 134 and bits, e.g., bits 150.1, 150.2, of a correspondingly large binary vector 150. The subset of the characters may be determined from the number of edit operations verified so far and/or a maximum edit distance. For instance, if two edit operations have been verified, this may imply that the current character (C) is one of the first three characters of the first string, so an inner product ($C=\delta_1 c_1 + \delta_2 c_2 + \delta_3 c_3$) involving only the first three characters of the first string may be computed. Similarly, if it is known that the edit distance between the first string and the second string is at most two and three edit operations have been verified, then it may be known that the current character must be the third or the fourth character, so an inner product involving only the third and fourth characters of the first string ($C=\delta_3 c_3 = \delta_4 c_4$) may be computed.

If first string 134 ($c_1, \ldots, c_n$) is a substring of a larger string 136 ($d_1, \ldots, d_{l_d}, c_1, \ldots, c_n, e_1, \ldots, e_{l_e}$) and current position 132 ($i$) in the first string is expressed as a current position in larger string 136 ($l_d + i$), then character matching unit 145 may determine character 151 at the current position 132 in the first string by computing an inner product ($C_1 = \langle \vec{\varepsilon}, \vec{d} \rangle = \varepsilon_1 d_1 + \ldots + \varepsilon_{l_d} d_{l_d}$) between zero or more characters ($d_1, \ldots, d_{l_d}$) of larger string 136 and a prefix binary vector ($\vec{\varepsilon}$) indicating which of the one or more characters is the character at the current position 132; computing an inner product ($C = \langle \vec{\delta}, \vec{c} \rangle = \delta_1 c_1 + \ldots + \delta_n c_n$), between one or more characters ($\vec{c}=(c_1, \ldots, c_n)$), e.g., characters 134.1, 134.2, of the first string 134 and a first binary vector 150 ($\vec{\delta}=(\delta_1, \ldots, \delta_n)$) indicating which of the one or more characters is the character at the current position, as above; computing an inner product ($C_2 = \langle \vec{\phi}, \vec{e} \rangle = \phi_1 e_1 + \ldots + \phi_{l_e} e_{l_e}$) between zero or more characters ($e_1, \ldots, e_{l_e}$) of the larger string 136 and a postfix binary vector ($\vec{\varepsilon}$) indicating which of the one or more characters is the character at the current position 132; and adding up the three inner products ($C' = C_1 + C + C_2 = \langle \vec{\varepsilon}, \vec{d} \rangle + \langle \vec{\delta}, \vec{c} \rangle + \langle \vec{\phi}, \vec{e} \rangle$). E.g., character matching unit 145 may compute an inner product ($\langle \vec{\varepsilon}; \vec{\delta}; \vec{\phi}, \rangle$) between one or more characters of larger string 136 ($\vec{d}; \vec{c}; \vec{e}$), e.g., including first string 134, and a binary vector ($\vec{\varepsilon}; \vec{\delta}; \vec{\phi}$) indicating which of the one or more characters is the character at current position 132. By including characters from larger string 136, data-obliviousness is further improved by making memory access patterns less reliant on the position ($l_d$) of first string 134 in larger string 136.

In order to determine character 161 at current position 133 in second string 135, character matching unit 145 computes an inner product ($D = \langle \vec{\varepsilon}, \vec{d} \rangle = \varepsilon_1 d_1 + \ldots + \varepsilon_l d_l$) between one or more characters ($\vec{d}=(d_1, \ldots, d_l)$), e.g., characters 135.1, 135.2, of second string 135 and a second binary vector 160 ($\vec{\varepsilon}=(\varepsilon_1, \ldots, \varepsilon_n)$) indicating which of the one or more characters is the character at current position 133 in the second string, e.g., $\delta_i$ is 1 if $c_i$ is the current character and 0 otherwise. As for the inner product to compute character 151, this inner product may be an inner product between all characters of second string 135 or a subset of them, for instance, if it is known that the current character must be in this subset, e.g., because of the number of operations processed so far, because of a bound on the edit distance, or for any other reason, or a superset. Since the inner product computation may access other characters in addition to the character at the current position 133 in the second string, using an inner product may reduce the dependence of the memory access pattern on the particular current position 133, hence improving data-obliviousness.

Various options are available for computing binary vectors 150 and 160. For instance, character unit 145 may compute each element of each binary vector individually in the plain by setting it to 1 if it corresponds to the current position 132 in the first string or 133 in the second string, respectively. In some embodiments, computation device 110 performs the validation computation as a multi-party computation, in which case known techniques e.g., using secret indexing as detailed below, may be used to compute binary vector 150 and/or 160. In some embodiments, computation device 110 performs the validation computation as a verifiable computation, in which case known techniques such as the zero-equality gate as detailed below, may be used to compute the elements of binary vector 150 and/or 160.

As discussed above, it can be beneficial for character matching unit 145 to set character 151 at the current position in the first string and/or character 161 at the current position in the second string to a special value in case their respective current positions 132, 133 are out-of-bounds, e.g., if they point to the character directly after first string 134, after larger string 136 which first string 134 is a substring, or after second string 135. Character matching unit 145 may determine character 151 at current position 132 in the first string by computing an inner product between one or more characters of first string 134 and a binary vector 150 indicating which of the one or more characters is the character at the current position, as discussed above, plus the special value multiplied by a bit indicating whether current position 132 in the first string is out of bounds e.g., whether current position 132 points at the character directly after first string 133 or larger string 136 of which it is a substring. E.g., character matching unit 145 determines character 151 by computing an inner product between one or more characters of first string 134 and binary vector 150 indicating which of the one or more characters is the character at current position 132 and adding to this result the special value multiplied by a bit indicating whether the current position 132 in first string 134 is out of bounds e.g., whether current position 132 points at the character directly after first string 134 or of larger string 136 of which first string 134 is a substring.

Similarly, character matching unit 145 may determine character 161 at current the position in the second string by computing an inner product between one or more characters of the second string 135, e.g., characters 135.1, 135.2, and a binary vector 160 indicating which of the one or more characters is the character at current position 133, as above, plus the special value multiplied by a bit indicating whether current position 133 in the second string is out of bounds e.g., whether it points at the character directly after the second string 135. E.g., character matching unit 145 computes character 161 at the current position in the second string by computing an inner product between one or more characters of the second string 135 and a binary vector 160 indicating which of the one or more characters is the character at current position 133 and adding to this result the special value multiplied by a bit indicating whether current position 133 in the second string is out of bounds e.g., whether it points at the character directly after the second string 135.

Although character matching unit 145 in FIG. 3 determines both character x, 151, at the current position in the first string and character w, 161, at the current position in the second string as inner products, in other embodiments, x and/or w may be computed using alternative methods, e.g., simply by performing a direct memory access at the location in the memory where the relevant character is stored.

Figure 4A:
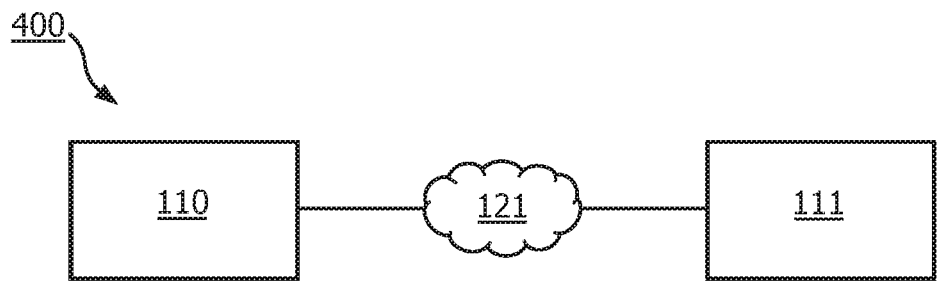
Figure 4B:
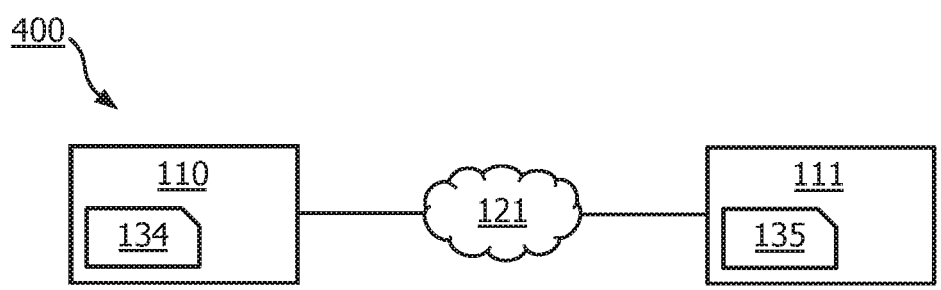
Figure 4C:
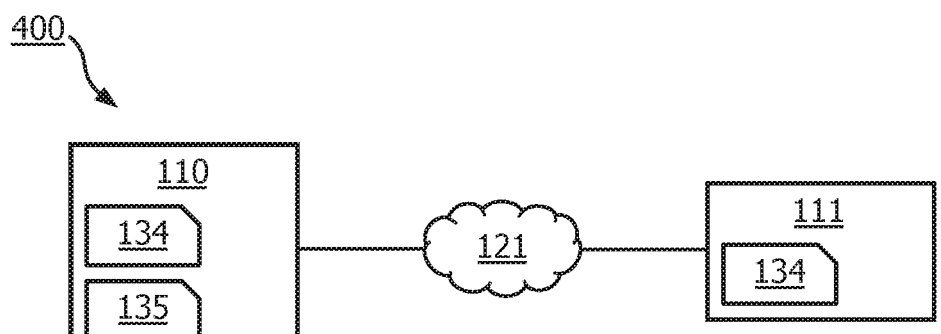

Multiple computation devices together may form an embodiment of a multiparty computation system for verifying that edit script is for transforming a first string to a second string. FIG. 4a-FIG. 4c schematically show various examples of embodiments of a multiparty computation system 400.

The various computation devices, e.g., computation devices 110, 111, of multiparty computation system 400 may communicate with each other over a computer network 121. The computer network may be an internet, an intranet, a LAN, a WLAN, etc. The computer network may be the Internet. The computer network may be wholly or partly wired, and/or wholly or partly wireless. For example, the computer network may comprise Ethernet connections. For example, the computer network may comprise wireless connections, such as Wi-Fi, ZigBee, and the like. Computation device 110 may comprise a communication interface 120, e.g., as in FIG. 1a, which is arranged to communicate with other devices of system 400 as needed. For example, the communication interface may comprise a connector, e.g., a wired connector, e.g., an Ethernet connector, or a wireless connector, e.g., an antenna, e.g., a Wi-Fi, 4G or 5G antenna. The computer network may comprise known elements such as, e.g., a router, a hub, etc. Communication may be in the form of digital messages, e.g., send and received in electronic form. Although not shown in FIG. 4a-FIG. 4c, apart from computation devices 110, 111, multiparty computation system 400 may be configured with additional computation devices.

The multiple computation devices, e.g., computation devices 110, 111, of multiparty computation system 400 may be configured to perform a MPC, or multi-party computation, protocol. For example, each of the multiple devices may have private data over which the multiple computation devices jointly perform a computation. For example, the devices may be configured to send and receive secret-shares of values, and to perform computations on the secret-shares. In particular, the validation computation may be performed as a multi-party computation between the computation device 110 and the one or more other computation devices, e.g., computation device 111. Advantageously, this may allow verification between multiple computation devices of multiple mutually distrusting parties without them needing to share their sensitive inputs, e.g., the first string or second string.

In some embodiments, known techniques for performing a MPC are used to perform the validation computation based on secret sharing, and at least one of the representations of one or more characters of the first string, the representations of one or more characters of the second string, the representation of the current position in the first string, the representation of the current position in the second string, and the representation of the edit script, is a secret-share of a secret-sharing between the computation device and the one or more other computation devices. For example, the devices may be configured to perform MPC based on the SPDZ protocol ("Multiparty Computation from Somewhat Homomorphic Encryption", I. Damgard and V. Pastro and N. P. Smart and S. Zakarias, Proceedings of CRYPTO 2012, included herein by reference) or based on Shamir secret sharing, e.g., using the building blocks from "Design of large scale applications of secure multiparty computation: secure linear programming", S. de Hoogh, PhD thesis from Eindhoven University of Technology, included herein by reference, or other known techniques. Alternatively, other MPC techniques may be used, e.g., based on garbled circuits or additively homomorphic encryption. In general, when performing a computation using MPC it is advantageous if the computation is data-oblivious since this allows the computation to take place while keeping sensitive data private, e.g., in secret-shared form. Hence performing the validation computation with MPC is particularly advantageous.

In particular, in an embodiment of a multiparty computation system 400 schematically shown in FIG. 4b, first string 134 is a private input to the multi-party computation of computation device 110 and second string 135 is a private input to the multi-party computation of computation device 111. For instance, computation device 110 may be configured to provide secret-shares of one or more of the characters of first string 134 to the other computation devices involved in the MPC, including computation device 111, and to receive secret-shares of one or more of the characters of second string 135 from computation device 111. Alternatively, second string 135 may be a private input to the multi-party computation of computation device 110 and first string 134 may be a private input to the multi-party computation of computation device 111. For instance, computation device 110 may be configured to provide secret-shares of one or more of the characters of second string 135 to the other computation devices involved in the MPC, including computation device 111, and to receive secret-shares of one or more of the characters of first string 134 from computation device 111. In some embodiments, the computation devices 110, 110 are further configured to generate the edit script by identifying allowable edit operations from the first and second string and adding said identified allowable edit operation to the edit script, a dummy operation being added to the edit script if a mismatch or insertion operation is added to the edit script, as detailed below. This may have as an advantage that the parties can jointly establish that there is an edit script for transforming the first string to the second string, e.g., satisfying certain desirable properties, with neither party needing access to the other party's input.

In an embodiment of a multiparty computation system 400 shown schematically in FIG. 4c, second string 135 may be a private input to the multi-party computation of computation device 110 or any of the other computation devices involved in the MPC, and first string 134 may be a public input to the multi-party computation. For instance, computation device 110 is configured to send or receive secret-shares of one or more of the characters in the second string 135, whereas the computation devices all have a plaintext representation of one or more of the characters of first string 134. In some embodiments, the edit script is also a private input to the multi-party computation of computation device 110. This has an advantage that the computation devices gain assurance that edit script held by computation device indeed is for transforming first string 134 to second string 135, without computation device 110 needing to share details about the edit script. In other embodiments, the edit script is generated by the computation devices or input by another computation device.

Apart from the particular ways that the input data is distributed in FIG. 4b or FIG. 4c, various other configurations will be apparent for the person skilled in the art; for instance, some of the characters of the first string may be a private input of computation device 110 and other characters of the first string may be a private input of computation device 111; and similarly, different computation devices may provide different parts of the second string as private input. In some embodiments, some or all of the characters of the first or second string are not directly input by any particular computation device but are instead themselves the result of a previous multi-party computation.

In general, performing edit script verification in a multi-party computation system 140 may allow computation device 110 to verify that an edit script is for transforming a first string into a second string without necessarily needing to have plaintext access to the entire first string, second string, and edit script, thereby providing a privacy advantage in systems where such an edit script verification is needed.

Figure 4D:
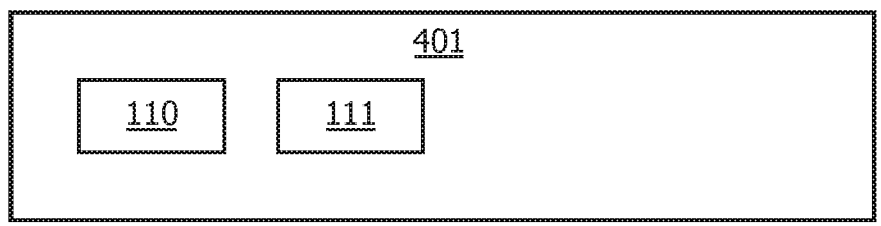

Instead of communication over a digital network 121, there are other ways to constitute a multiparty computation system. For example, FIG. 4d schematically shows an example of an embodiment of a multiparty computation system 401. In system 401 multiple computation devices, or units 110, 111, are comprised in a single larger device 401. For example, these may be applications and/or hardware elements that are mutually mistrustful of each other. In case of system 401, the communication interface may be an intra-device communication interface, a function call, an API, a bus, etc.

Figure 5A:
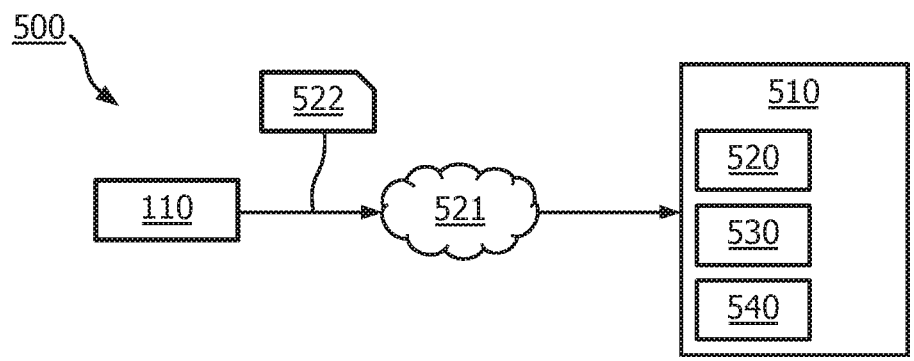
Figure 5B:
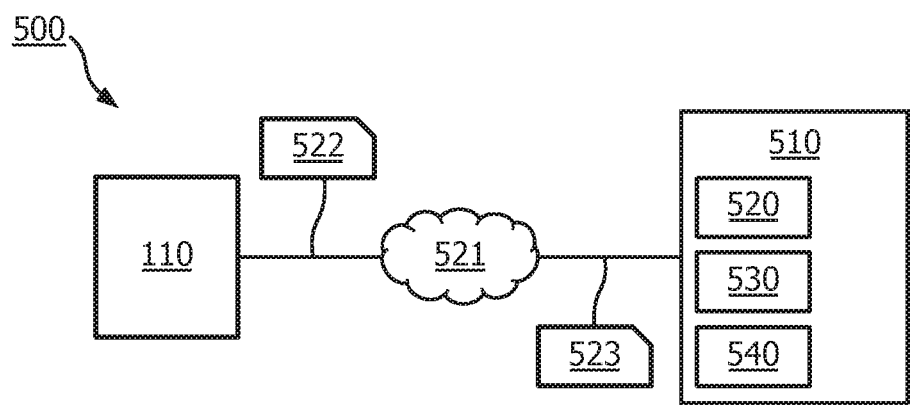
Figure 5C:
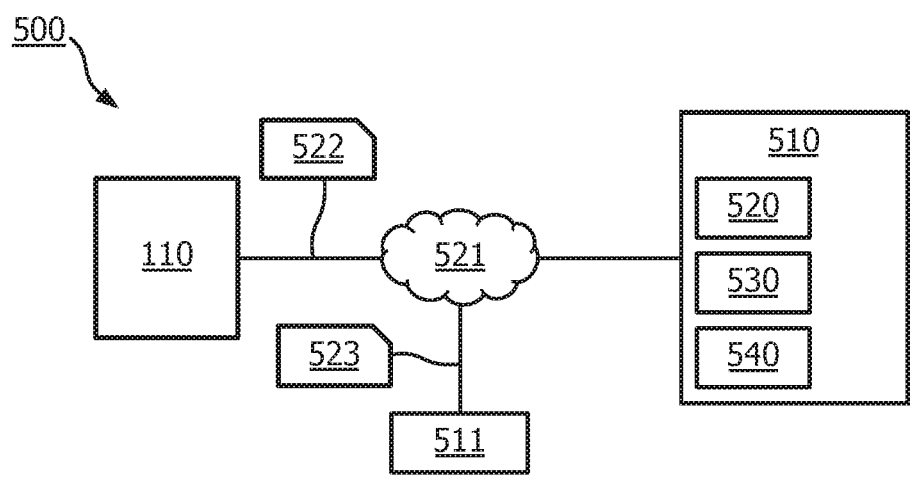

FIG. 5a-FIG. 5c schematically show various examples of embodiments of a verifiable computation system 500 for verifying that an edit script is for transforming a first string to a second string, comprising computation device 110 and a verification device 510. Verification device 510 may comprise a memory 530 and a processor 540. Memory 530 may be used for data and/or instruction storage. For example, memory 530 may comprise software and/or date on which processor 540 is configured to act. Processor 540 may be implemented as one or more processor circuits, e.g. microprocessors, ASICs, FPGA and the like. Memory 530 may comprise computer program instructions which are executable by processor 540. Processor 540, possibly together with memory 530 is configured according to an embodiment of a verification device. In any of the figures FIG. 5a-FIG. 5c, computation device 110, verification device 510, and optionally data providing device 511 may communicate with each other over a computer network 521. Communication network 521 may be configured similarly to communication network 121 described above. Communication interfaces 140, 540 of computation device 110 and verification device 510 may be configured similarly to the communication interface in FIG. 1b. In embodiments schematically shown in FIG. 5c, verifiable computation system 102 additionally comprises a data providing device 511 that we discuss in more detail below.

In some embodiments, e.g., as above in FIG. 5a-FIG. 5c, the validation computation executed on computation device 110 is performed as a verifiable computation generating a cryptographic verifiable computation proof 522 that the validation computation was performed successfully. Computation device 110 is further configured to provide the cryptographic proof 522 to verification device 510. Various techniques for performing verifiable computations are known from the literature, e.g., the Pinocchio system ("Pinocchio: Nearly Practical Verifiable Computation" by B. Parno, J. Howell, C. Gentry and M. Raykova, proceedings of IEEE Security & Privacy 2013, included herein by reference) or the Buffet system ("Efficient RAM and control flow in verifiable outsourced computation", R. Wahby, S. Setty, Z. Ren, A. Blumberg, M. Walfish", proceedings of the 2015 Network and Distributed System Security symposium, included herein by reference). In some embodiments, the verifiable computation generating the cryptographic proof 522 is itself executed in a distributed way, for example, as a multi-party computation using techniques known from the literature such as the Trinocchio system ("Trinocchio: Privacy-Preserving Outsourcing by Distributed Verifiable Computation", B. Schoenmakers, M. Veeningen, and N. de Vreede, Applied Cryptography and Network Security, ACNS 2016, included herein by reference). Using systems like Pinocchio, Buffer, or Trinocchio, data-obliviousness is advantageous since it allows computations with different inputs to use the same key material and/or proof generation procedure and/or proof verification procedure, and it allows the proofs for different inputs to look similar, e.g., based on the zero-knowledge variants of the systems quoted above. Hence performing validation computation according to some of the embodiments outlined above as a verifiable computation is particularly advantageous.

Cryptographic verifiable computation proof 522 that the validation computation was performed may be with respect to plain inputs and outputs. The plain inputs and outputs in this setting may comprise one or more characters of the first string 134 and/or one or more characters of the second string 135 and/or one or more characters of the edit script 131. The first string may also be a substring of a larger string occurring as a data block in a Merkle hash tree, in which case the plain inputs and outputs may comprise the root of the Merkle hash tree. Note that the first string, second string, and edit script are not necessarily inputs or outputs to the verifiable computation proof, e.g., if the proof comprises additional computations and the edit script verification occurs gets its inputs and/or provides its outputs to such additional computations.

Apart from plain inputs and outputs, for instance, as in the Pinocchio system, verifiable computation proof 522 may also be with respect to other input/output representations. Various ways of representing inputs and/or outputs to a verifiable computation proof are known from the literature, e.g., as authenticated data ("ADSNARK: Nearly Practical and Privacy-Preserving Proofs on Authenticated Data", M. Backes, M. Barbosa, D. Fiore and R. Reiscuk, proceedings the 2015 IEEE Symposium on Security and Privacy, included herein by reference), as hashes ("Hash First, Argue Later: Adaptive Verifiable Computations on Outsourced Data", D. Fiore, C. Fournet, E. Ghosh, M. Kohlweiss, O. Ohrimenko, B. Parno, proceedings of the 2016 ACM SIGSAC Conference on Computer and Communications Security, included herein by reference), or as commitments ("Pinocchio-Based Adaptive zk-SNARKs and Secure/Correct Adaptive Function Evaluation", M. Veeningen, Progress in Cryptology—AFRICACRYPT 2017, included herein by reference). Any of the inputs or outputs to the verifiable computation proof, e.g., characters of the first string, characters of the second string, a larger string of which the first string is a substring, the root of a Merkle hash tree in which the larger string occurs as a data block, may use such a representation, e.g., any one of them may be represented as authenticated data, a hash, a commitment, or using any other representation. For example, verifiable computation proof 522 may be with respect to a representation of the one or more characters of the first string as a commitment, hash, or authenticated data, and with respect to one or more characters of the second string as plain inputs. Or, the first string may be a substring of a larger string, the larger string occurring as a data block in a Merkle hash tree, and verifiable computation proof 522 may be with respect to a plain representation of the root of this hash tree and a commitment representation of the characters of the second string.

Generating the cryptographic verifiable computation proof 522 may use an evaluation key that depends on particular characteristics of the validation computation performed. For example, the evaluation key may depend on the length of the first string and/or the length of the second string and/or a maximum edit distance between the first string and the second string. It may also, for instance, depend on which representations are used for the inputs and outputs to the verifiable computation. The evaluation key may be generated or provided by verification device 510 or by any other device. It may also be hardcoded into computation device 510, for example as a system parameter.

Verification device 510 schematically shown in FIG. 5*a*-FIG. 5*c* is configured to receive cryptographic verifiable computation proof 522 from computation device 110 and verify the proof. Various techniques for verifying proof 522 are known from the literature, e.g., using the Pinocchio or Buffet systems mentioned earlier. Verifying the proof 522 may use a verification key that, like the evaluation key, depends on particular characteristics of the validation computation performed, e.g., the length of the first and/or second string and/or a maximum edit distance. The evaluation key may be generated by verification device 510 itself, provided by another device, or hardcoded into the device 510 itself. The cryptographic verifiable computation proof 522 received from computation device 110 is a proof a that a validation computation was performed successfully, the validation computation comprising, for each edit operation in the edit script:

if the edit operation is a match operation, determining the character at the current position in the first string and the character at the current position in the second string, verifying that they match, incrementing the current position in the first string by one and incrementing the current position in the second string by one, if the edit operation is a difference operation, incrementing the current position in the first string and/or the current position in the second string by one.

As a consequence, verifying the proof may comprise verifying that an edit script is for transforming a first string to a second string.

Verification device 510 may verify verifiable computation proof 522 with respect to various types of representations, e.g., plain, as authenticated data, as hashes, or as commitments, using the techniques known from the literature indicated above. Different inputs, e.g., characters of the first string, characters of the second string, the edit script, the root of a Merkle hash tree, or any other input or output, may be represented in different ways. For example, verification device 510 may verify verifiable computation proof 522 with respect to a committed representation of the characters of the first string and a plain representation of the characters of the second string.

In particular, verifiable computation proof 522 may be with respect to an input representation 523 by a data providing device of the first string, of a larger string of which it is a substring, or of the root of a Merkle hash tree having the larger string as a data block. The input representation may be a plain input representation, e.g., a plain representation of the root of Merkle hash tree, or another type of representation, e.g., a hash, a commitment, or an authenticated data representation of the first string or the larger string. A different input representation 523 may be used for the verification of for each computation proof 522, or multiple proofs 522 may be with respect to the same input representation 523. In some embodiments shown schematically in FIG. 5*b*, verification device 510 is further configured to receive the input representation 523 and verify that it has been authenticated by the data providing device. For example, verification device 510 may verify correctness of a digital signature on the input representation with respect to a public key of the data providing device. Verification device 510 may receive input representation 523 from computation device 110 or from any other source, for instance, a website. In some embodiments shown schematically in FIG. 5*c*, verification device 510 is further configured to receive input representation 523 from data providing device 511.

Returning to FIG. 2 and FIG. 3. Below details are given of algorithm VerifyEditScript (Algorithm 1) performing a validation computation according to some embodiments shown schematically in FIG. 2 and/or FIG. 3. Variables between brackets denote non-public values with respect to which the algorithm improves data-obliviousness.

---

Algorithm 1. Edit script verification

---

Require: [X]: larger string 136 of which first string 134 is a substring, [W]: second string 135, [xpos]: position of first string in X, z: maximum edit distance, e.g., maximum number of mismatches, [S]: edit script 131 of length len([W]) + z
Ensure: assert an error if edit script 131 is not for transforming first string 134 to second string 135, otherwise returns

```
1:    function VerifyEditScript([X]; [W]; [xpos]; z; [S])
2:        [wpos] ← 1
3:        [nerrors] ← 0
4:        for i = 1,...,len([S]) do
5:            [ismatch] ← ([Si] = match)
6:            [ismismatch] ← ([Si] = mismatch)
7:            [isinsertion] ← ([Si] = insertion)
8:            [isdeletion] ← ([Si] = deletion)
9:            [nerrors] ← [nerrors] + [ismismatch] + [isinsertion] + [isdeletion]
```

-continued

Algorithm 1. Edit script verification

```
10:     assert([nerrors] ≠ z + 1)
11:     assert([xpos] ≠ len([X]) + 2)
12:     assert([wpos] ≠ len([W]) + 2)
13:     [x] ← ([X]||[0])[xpos]
14:     [w] ← ([W]||[0])[wpos]
15:     [err] ← [match]·([x=0]+ [w=0]+ [x−w≠0])+ [mismatch]·([x=0]+ [w=0])
16:     assert([err] = 0)
17:     [xpos] ← [xpos] + [ismatch] + [ismismatch] + [isdeletion]
18:     [wpos] ← [wpos] + [ismatch] + [ismismatch] + [isinsertion]
19:  assert([wpos] = len([W]) + 1)
```

Algorithm 1 may be performed in a privacy-preserving way, e.g., as a multi-party computation using any framework for multiparty computation, e.g., VIFF, available, e.g., at http://viff.dk or http://www.win.tue.nl/~berry/TUeVIFF/. In this case, asserts may be performed by public zero tests, as available in VIFF, and secret indexing $[c] \leftarrow [A]_{[b]}$ is done as described in, e.g., "Design of large scale applications of secure multiparty computation: secure linear programmming", S. de Hoogh, PhD thesis from Eindhoven University of Technology. In particular, [c] may be computed by computing an inner product between [A] and a binary vector indicating which of the characters of [A] is the character at position [b].

Alternatively, Algorithm 1 may be performed as a verifiable computation, for instance using the VIFF-based framework from "Pinocchio-Based Adaptive zk-SNARKs and Secure/Correct Adaptive Function Evaluation", M. Veeningen, Progress in Cryptology—AFRICACRYPT 2017, included herein by reference. In this case, the production of the verifiable computation proof 522, e.g., performing the verifiable computation generating a cryptographic verifiable computation proof, may be performed in a privacy-preserving way, e.g., in a distributed way using multi-party computation, or not. Note that "Pinocchio-Based Adaptive zk-SNARKs and Secure/Correct Adaptive Function Evaluation" details oblivious construction for arithmetic computations and the operator $[b] \leftarrow [a] \neq 0$, also known as a zero-equality gate. Based on this, the operations used in Algorithm 1 may be implemented as follows:

$[a] \leftarrow ([b]=c)$ may be computed as $[a] \leftarrow 1-([b-c] \neq 0)$ assert($[a] \neq b$) may be done by computing $[x] \leftarrow [(a-b) \neq 0]$, opening x and checking it is zero assert($[a]=0$) may be done by opening a and checking it is zero computing $[c] \leftarrow [A]_{[b]}$ may be done by converting [b] into unit, e.g., binary vector ($[b_1], \ldots, [b_{len([A])}]$), with 1 at position [b], proving its correctness by checking that $[b_i]$ equals ($[b]=i$) for all i, and computing an inner product $[c] \leftarrow [b_1] \cdot [A_1] + [b_2] \cdot [A_2] + \ldots$ between characters $[A_1], [A_2], \ldots$ of [A] and binary vector ($[b_1], \ldots [b_{len([A])}]$) indicating which of the characters $[A_1], [A_2], \ldots$ is the character at position [b].

Algorithm 1 goes through the elements $[S_i]$ 131.1, 131.2 of edit script 131, keeping track of the current location [xpos], 132, in first string 134, expressed as a current position in larger string 136 and [wpos], 133, in second string 135. It is advantageous to check that the number of errors does not exceed the bound z; this is done by checking inside the loop that the number of errors [nerrors] encountered so far does not equal z+1 (line 10). Alternatively, one can verify that [nerrors] ≤z at the end. It is also advantageous to check that the current positions in larger string X, 136, and second string W, 135, do not exceed their bounds. However, the current position 132, 133, may be allowed to be the length plus one, e.g., in case no match or mismatch occurs in edit script 131 that requires a read at this location. Hence, Algorithm 1 checks that the current position 132, 133, never reaches the length plus two (lines 11 and 12).

Algorithm 1 then computes the characters [x], 151, and [w], 161, at the given locations. In particular, character [x], 151, at current position [xpos], 132, in the first string may 134 may be computed by computing an inner product between one or more characters, e.g., characters 134.1, 134.2, of first string 134 and a first binary vector 150 indicating which of the one or more characters, e.g., characters 134.1, 134.2, is the character at the current position, where the inner product is combined with an inner product, e.g., when Algorithm 1 is performed as a multi-party computation or as a verifiable computation. In Algorithm 1, this inner product may be computed as part of a larger inner product between a binary vector and larger string [X], 136, to which a zero is appended, e.g., to allow current position 132 in the first string to be expressed as a current position in larger string [X], 136, and/or to allow the operation in line 13 to succeed also when current position [xpos], 132, is out-of-bounds, as discussed above. Similarly, character [w] at current position [wpos], 133 in second string 135 may be computed by computing an inner product between one or more characters [W], e.g., characters 135.1, 135.2, of second string 135 and a second binary vector 160 indicating which of the one or more characters, e.g., characters 135.1, 135.2, is the character at the current position. In Algorithm 1, this inner product may be computed as part of a larger inner product between a binary vector and second string [W], 135, to which a zero is appended, to allow the operation in line 14 to succeed also when current position [wpos], 133, is out-of-bounds, as discussed above.

Algorithm 1 then checks if there is an error in edit script 131, which may be the case if there is supposed to be a match and [x], 151, and [w], 161, do not match or are outside of the strings 134, 136; or if there is supposed to be a mismatch and [x], 151, or [w], 161, is outside of the string 134, 136 (line 16). Finally, Algorithm 1 checks that the edit script 131 has reached the end of the second string 135 (line 19). These checks combined may indicate validity of the edit script 131, e.g., second string 135 did occur at the given location in larger string 136 of which first string 134 is a substring with an edit distance of at most z.

Returning to FIG. 2. In some embodiments, computation device 110 is further configured to generate edit script 131 by identifying allowable edit operations from the first string 134 and second string 135 and adding said identified allowable edit operation to edit script 131, a dummy operation being added to edit script 131 if a mismatch or insertion operation is added to edit script 131. For instance, computation device 110 may be configured with a maximum edit distance, the edit distance comprising the Levenshtein distance, and the set of allowed edit operations comprising match operations, mismatch operations, insertion operations, deletion operations, and dummy operations. The number of edit operations that edit script 131 comprises after generation may then be equal to the length of the second string plus the maximum edit distance. While generating edit script 131, computation device 110 may identify that a match operation is an allowable edit operation and add this operation to the edit script. This increases the length of edit script 131 by one, the number of characters of second string 135 consumed by one, and the number of errors consumed by zero. Similarly, computation device 110 may identify that a deletion operation is allowable and add it to edit script 131. This increases the length of edit script 131 by one, the number of characters of second string 135 consumed by zero, and the number of errors consumed by one.

Computation device 110 may also identify that a mismatch operation is allowable and add it to edit script 131. This increases the number of characters of second string 135 consumed by one and the number of errors consumed by one. In such a case, it may be advantageous for getting edit script 131 that is of the desired length in a more data-oblivious way to add a dummy operation if a mismatch operation is added so that the length of edit script 131 may be increased by the same amount as the increase in characters and errors consumed, e.g., by two. Computation device 110 may also identify that an insertion operation is allowable and add it to edit script 131. This increases the number of characters of second string 135 consumed by one and the number of errors consumed by one. Hence it may be advantageous for getting edit script 131 of the right length to add a dummy operation if an insertion operation is added so that the length of edit script 131 may be increased by the same amount as the increase in characters and errors consumed, e.g., by two.

It is not necessary that generated edit script 131 comprises mismatch, insertion, and deletion operations, or that the edit distance comprises the Levenshtein distance. For example, edit script 131 may only comprise match, mismatch, and dummy operations, or it may comprise additional operations such as swapping operations. In any case, computation device 110 is preferably configured such that the desired number of operations in edit script 131 is sufficient for transforming any appropriate first string 134 to any appropriate second string 135 within the maximum edit distance. Moreover, a number of dummy operations is preferably added to edit script 131 for each added edit operation depending on the type of the edit operation in such a way that the right number of operations in edit script 131 is attained after all identified allowable edit operations have been added to edit script 131.

Regardless of how edit script 131 is verified, e.g., as a multi-party computation or a verifiable computation, generating edit script 131 may be performed in various ways. For instance, generating edit script 131 may be performed in the plain or in a distributed fashion with other computation devices, e.g., computation device 111, in a privacy-preserving way, e.g., using multi-party computation. Algorithm 2 is used in some embodiments to generate edit script 131 for transforming a first string 134 to a second string 135, where the algorithm searches first string 134 in a larger string 136. Algorithm 2 provides advantages from a data-obliviousness point of view, for instance, by adding dummy operations which may help to ensure that generated edit script 131 has a length that is a function of the length of first string 134, the length of second string 135, and a maximum edit distance.

---

Algorithm 2 Inexact search

---

Require: X: larger string 136, [W]: unmatched part of second string 135, R: matched part of second string 135, z: number of allowed mismatches, e.g., maximum Levenshtein edit distance
Ensure: Returns ([f]; [p]; [S]) where, if the second string 135 does not occur with maximum edit distance z in the larger string, then f = 0; otherwise, f = 1, p is the position of the second string 135, and S the corresponding edit script 131

1:   function InexRecur(X; [W]; R; z)
2:   if len([W]) = 0 then // empty search string: we have found a match
3:       p ← location of any occurence of R in X
4:       return ([1]; [p]; ([dummy; ... ; dummy])) // z dummies
5:   ([W']; [w]) ← [W] // split into last character and remainder
6:   ([f]; [p]; [S]) ← ([0]; [0]; ([dummy; ... ; dummy])) // z + len([W]) dummies
7:   if z > 0 then
8:       ([f']; [p']; [S']) ← InexRecur(X; [W']; R; z − 1) // insertion
9:       ([f]; [p]; [S]) ← Combine(([f]; [p]; [S]); ([f']; [p']; [insertion]||[dumm]||[S0]))
10:  for c ∈ {A,C,G,T} do
11:      if b||R occurs in X then
12:          if z > 0 then // deletion
13:              ([f']; [p']; [S']) ← InexRecur(X; [W]; b||R; z − 1)
14:              ([f]; [p]; [S]) ← Combine(([f]; [p]; [S]); ([f']; [p']; [deletion]||[S']))
15:          ([f1]; [p1]; [S1]) InexRecur(X; [W']; b||R; z) // match
16:          [S1] ← [match]||[S1]
17:          if z > 0 then // mismatch
18:              ([f2]; [p2]; [S2]) ← InexRecur(X; [W']; b||R; z − 1)
19:              [S1] ← [mismatch]||[dummy]||[S1]
20:          else
21:              ([f2]; [p2]; [S2]) ← ([0]; [0]; ([dummy; ...; dummy])) // z + len([W])×
22:          ([f']; [p']; [S']) ← CCombine([w] = b; ([f1]; [p1]; [S1]); ([f2]; [p2]; [S2]))
23:          ([f]; [p]; [S]) ← Combine(([f]; [p]; [S]); ([f']; [p']; [S']))
24:  return ([f]; [p]; [S])
Require: ([f]; [p]; [S]); ([f']; [p']; [S']): two InexRecur return values
Ensure: Returns ([f]; [p]; [S]) if f = 1, ([f']; [p']; [S']) otherwise
25:  function Combine(([f]; [p]; [S]); ([f']; [p']; [S']))
26:      return ([f]+ [f'] − [f] · [f']; [f] · [p]+ (1 − [f]) · [p]; ([f] · [S1]+ (1 − [f] · [S'1 ]; ...))
Require: [b]: choice bit, ([f]; [p]; [S]); ([f']; [p']; [S']): two InexRecur return values -continued Algorithm 2 Inexact search Ensure: Returns ([f]; [p]; [S]) if b = 1, ([f']; [p']; [S']) otherwise
27:  function CCombine([b]; ([f]; [p]; [S]); ([f']; [p']; [S']))
28:    return ([b]·[f]+(1−[b])·[f']; [b]·[p]+(1−[b])·[p]; ([b]·[S1]+ (1−[b]·[S'1 ]; ...))

Algorithm 2 may be implemented in a privacy-preserving way using any framework for multiparty computation, e.g., VIFF, available, e.g., at http://viff.dk or http://www.win.tu-e.nl/~berry/TUeVIFF/. Alternatively, Algorithm 2 may be implemented in a non-privacy-preserving way to get an algorithm for inexact search that returns edit script 131, including dummy operations, as well as returning the search result. In this case, the conditional combine in line 22 may be replaced by calling InexRecur either for the match or the mismatch case, as appropriate.

The description above does not specify in detail how the actual searching in the larger string 136 happens (lines 11 and 3). Several possibilities will be apparent, e.g., using linear search or with a Burrows-Wheeler matrix, as detailed in "Fast and accurate short read alignment with Burrows-Wheeler transform", H. Li and R. Durbin, Bioinformatics, 25(14):1754-1760, 2009. Algorithm 2 is specific to strings consisting of characters A, C, G, and T, e.g., to DNA or other nucleic acid sequences; however, it will be apparent to a person skilled in the art how to generalize the algorithm to larger alphabets and how to apply the principle of computing edit script 131 while searching to other search algorithms. Focusing on how edit script 131 is computed, it is ensured that edit script 131 has length len([W])+z by its initialization (lines 4 and 6) and via the recursive calls for insertion (line 9), deletion (line 14), match (line 16), and mismatch (line 19). Note the algorithm adds a dummy operation to edit script 131 if a mismatch or insertion operation is added to edit script 131, but not for deletion and mismatch operations. Results from multiple recursive calls are combined using the Combine function, that, given two return values, takes the first one if it represents a match and otherwise the second one, hence improving data-obliviousness. For the case of match and mismatch operations, data-obliviousness is improved by evaluating both the match and the mismatch branch and obliviously combining them with CCombine, which selects the match or mismatch result depending on the test [w]=b, which may be oblivious.

In embodiments based on a variant of Algorithm 2, edit script 131 may be generated using a search algorithm based on multi-party computation that keeps X private. In such embodiments, lines 11 and 3 may be evaluated in a privacy-preserving way based on private X. For instance, embodiments may always evaluate the "if" branch in line 12 and then ignore its result depending on the oblivious condition that b∥R occurs in [X]. It will be apparent to a person skilled in the art how Algorithm 2 can be modified accordingly using known techniques.

Figure 6:
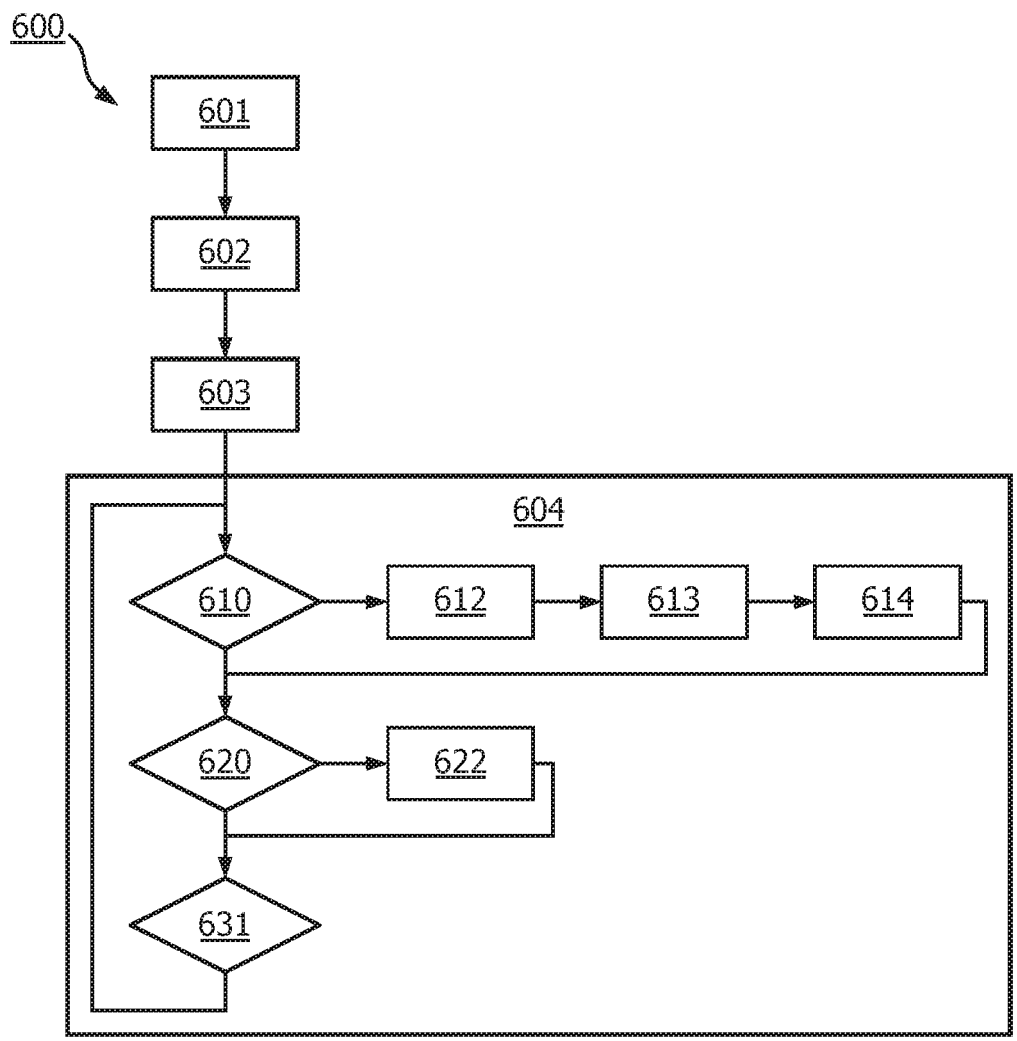

FIG. 6 schematically shows an example of an embodiment of a computation method 600. Computation method 600 is arranged for verifying that an edit script is for transforming a first string to a second string, the edit script comprising one or more edit operations, the edit operations being selected from a set of allowed edit operations, the set of allowed edit operations comprising match operations and difference operations. Computation method 600 comprises
    storing 601 a representation of one or more characters of the first string, a representation of one or more characters of the second string, a representation of a current position in the first string, and a representation of a current position in the second string,
    obtaining 602 a representation of the edit script, storing 603 the representation in the memory, and subsequently performing a validation computation 604, the validation computation 604 comprising, as long as not all edit operations have been processed 631:
        if the edit operation is a match operation 610, determining 612 the character at the current position in the first string and the character at the current position in the second string, verifying 613 that they match, and incrementing 614 the current position in the first string and the current position in the second string by one,
        if the edit operation is a difference operation 620, incrementing 622 the current position in the first string and/or the current position in the second string by one.

In some embodiments, character matching steps 612, 613, 614 may be performed not just if the edit operation is a match operation 610, but also for other edit operations. In such a case, computation method 600 may involve combining the outcome of check 610 and the results of steps 612, 613, 614 so that, steps 612, 613, 614 may be performed but their outcomes are effectively ignored for non-match operations. Similarly, incrementing step 622 may be performed not just if the edit operation is a difference operation 620, but also if it is not a difference operation, and the outcomes of check 620 and incrementing step 622 may be combined so that, even if step 622 if performed, its outcome may be ignored for non-difference operations. This may improve the data-obliviousness of the method by reducing the variation in memory access patterns for different edit operations.

Many different ways of executing the method are possible, as will be apparent to a person skilled in the art. For example, the order of the steps can be varied or some steps may be executed in parallel. Moreover, in between steps other method steps may be inserted. The inserted steps may represent refinements of the method such as described herein or may be unrelated to the method. For example, verifying 613 and incrementing 614 may be executed, at least partially, in parallel. Moreover, a given step may not have finished completely before a next step is started.

Embodiments of the method may be executed using software, which comprises instructions for causing a processor system to perform method 600. Software may only include those steps taken by a particular sub-entity of the system. The software may be stored in a suitable storage medium, such as a hard disk, a floppy, a memory, an optical disc, etc. The software may be sent as a signal along a wire, or wireless, or using a data network, e.g., the Internet. The software may be made available for download and/or for remote usage on a server. Embodiments of the method may be executed using a bitstream arranged to configure programmable logic, e.g., a field-programmable gate array (FPGA), to perform the method.

It will be appreciated that the invention also extends to computer programs, particularly computer programs on or in a carrier, adapted for putting the invention into practice. The program may be in the form of source code, object code, a code intermediate source, and object code such as partially compiled form, or in any other form suitable for use in the implementation of an embodiment of the method. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth.

Figure 7A:
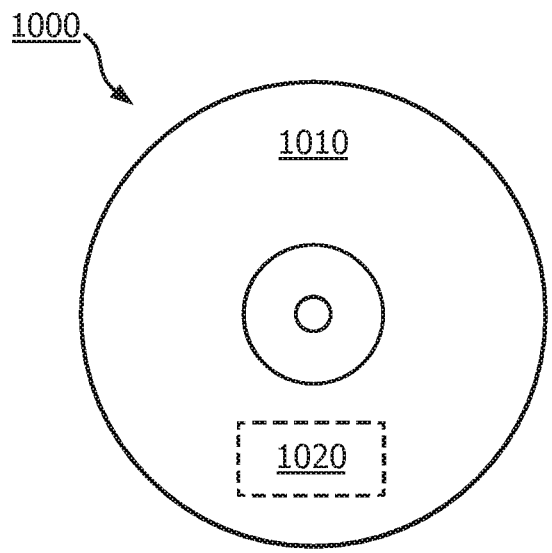

FIG. 7a shows a computer readable medium 1000 having a writable part 1010 comprising a computer program 1020, the computer program 1020 comprising instructions for causing a processor system to perform a computation method according to an embodiment. The computer program 1020 may be embodied on the computer readable medium 1000 as physical marks or by means of magnetization of the computer readable medium 1000. However, any other suitable embodiment is conceivable as well. Furthermore, it will be appreciated that, although the computer readable medium 1000 is shown here as an optical disc, the computer readable medium 1000 may be any suitable computer readable medium, such as a hard disk, solid state memory, flash memory, etc., and may be non-recordable or recordable. The computer program 1020 comprises instructions for causing a processor system to perform said computation method.

Figure 7B:
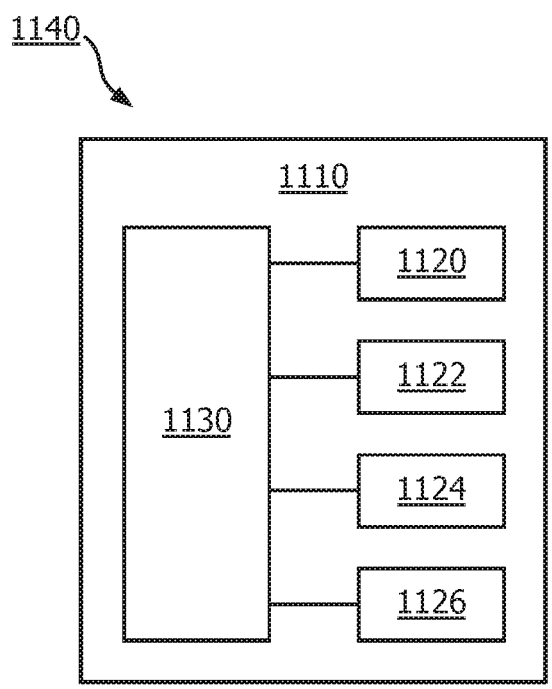

FIG. 7b shows in a schematic representation of a processor system 1140 according to an embodiment of a computation device. The processor system comprises one or more integrated circuits 1110. The architecture of the one or more integrated circuits 1110 is schematically shown in FIG. 4b. Circuit 1110 comprises a processing unit 1120, e.g., a CPU, for running computer program components to execute a method according to an embodiment and/or implement its modules or units. Circuit 1110 comprises a memory 1122 for storing programming code, data, etc. Part of memory 1122 may be read-only. Circuit 1110 may comprise a communication element 1126, e.g., an antenna, connectors or both, and the like. Circuit 1110 may comprise a dedicated integrated circuit 1124 for performing part or all of the processing defined in the method. Processor 1120, memory 1122, dedicated IC 1124 and communication element 1126 may be connected to each other via an interconnect 1130, say a bus. The processor system 1110 may be arranged for contact and/or contact-less communication, using an antenna and/or connectors, respectively.

For example, in an embodiment, processor system 1140, e.g., the computation device may comprise a processor circuit and a memory circuit, the processor being arranged to execute software stored in the memory circuit. For example, a processor circuit may be an Intel Core i7 processor, ARM Cortex-R8, etc. In an embodiment, the processor circuit may be ARM Cortex M0. The memory circuit may be an ROM circuit, or a non-volatile memory, e.g., a flash memory. The memory circuit may be a volatile memory, e.g., an SRAM memory. In the latter case, the device may comprise a non-volatile software interface, e.g., a hard drive, a network interface, etc., arranged for providing the software.

Embodiments are applicable in various settings, for example:

(A) A client lets a search for a second string be performed by third party and wishes to obtain a guarantee that the search result is correct, e.g., that a first string occurs as a substring in a larger string and there is an edit script for transforming the first string into the second string with a maximum edit distance, without having access to the larger string. The client may or may not have access to the first string and/or the second string, and/or it may be too resource-constrained to perform the search itself. In such settings, it may be advantageous to arrange a verification device of the client and a computation device of the third party in a verifiable computation system according to an embodiment.

(B) Same as (A), but where the search is performed in a privacy-preserving way using multi-party computation such that the parties carrying out the search do not need to learn the second string and/or the first string and/or the larger string they are searching in. For this it may be advantageous to arrange a verification device of the client and a computation device of the third party possibly with additional computation devices in a verifiable computation system according to an embodiment wherein the computation device is configured to generate a cryptographic proof in a distributed way, e.g., using multi-party computation.

(C) Same as (A), but where instead of by a non-interactive verifiable computation, the verification is performed by an interactive multi-party computation protocol between the client and the third party. For this it may be advantageous to arrange a computation device of the client and a computation device of the third party in a multiparty computation system according to an embodiment.

(D) A search is performed in a privacy-preserving way between several parties, e.g., one holding a larger string and another holding a second string where the objective is to find a first string that is a substring of the larger string such that there is an edit script for transforming the first string to the second string with a maximum edit distance. For efficiency reasons, the search may be performed using a protocol for multi-party computation that is passively secure but actively private, e.g., a protocol that prevents leakage of information to malicious participants but does not guarantee correctness. To obtain active security, e.g., a guarantee of correctness of the result, it may be advantageous for the parties to form an embodiment of a multiparty computation system for verifying that the edit script is for transforming the first string to the second string according to an embodiment, wherein an actively secure multiparty computation technique is used.

(E) A party wants to prove in a privacy-preserving way that a second string occurs with a certain maximal edit distance in a larger string from a data providing device. For instance, the data providing device may be a home genome sequencing device and the party may be a person who wants to prove to a third party that his or her genomic data satisfies certain properties, e.g., contains a first string that has a certain maximal edit distance to the second string, without disclosing the genome or the contents of the first string. Such settings may benefit from arranging a computation device and data providing device of the user and a verification device of the third party in a verifiable computation system according to an embodiment.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb 'comprise' and its conjugations does not exclude the presence of elements or steps other than those stated in a claim. The article 'a' or 'an' preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

In the claims references in parentheses refer to reference signs in drawings of exemplifying embodiments or to formulas of embodiments, thus increasing the intelligibility of the claim. These references shall not be construed as limiting the claim.

The invention claimed is:

1. A computation device configured to verify that an edit script is for transforming a first string to a second string, the edit script comprising one or more edit operations, the edit operations being selected from a set of allowed edit operations, the set of allowed edit operations comprising match operations and difference operations, the computation device comprising:
    a memory configured to store a representation of one or more characters of the first string, a representation of one or more characters of the second string, a representation of a current position in the first string, and a representation of a current position in the second string,
    a processor configured to obtain a representation of the edit script, store the representation in the memory, and subsequently perform a validation computation, the validation computation comprising, for each edit operation in the edit script:
        if the edit operation is a match operation, determining the character at the current position in the first string and the character at the current position in the second string, verifying that they match, incrementing the current position in the first string by one and incrementing the current position in the second string by one,
        if the edit operation is a difference operation, incrementing the current position in the first string and/or the current position in the second string by one.

2. A computation device as in claim 1, wherein the difference operations comprise mismatch operations, insertion operations and deletion operations, incrementing if the edit operation is a difference operation comprising:
    if the edit operation is a mismatch operation, incrementing the current position in the first string and the current position in the second string by one,
    if the edit operation is an insertion operation, incrementing the current position in the second string by one,
    if the edit operation is a deletion operation, incrementing the current position in the first string by one.

3. A computation device as in claim 1, wherein:
    determining the character at the current position in the first string comprises computing an inner product between one or more characters of the first string and a first binary vector indicating which of the one or more characters is the character at the current position, and/or
    determining the character at the current position in the second string comprises computing an inner product between one or more characters of the second string and a second binary vector indicating which of the one or more characters is the character at the current position.

4. A computation device as in claim 1, wherein the first string is a substring of a larger string, the current position in the first string being expressed as a current position in the larger string.

5. A computation device as in claim 4, wherein the validation computation further comprises verifying that the larger string occurs as a data block in a Merkle hash tree.

6. A computation device as in claim 1, wherein the computation device further comprises a communication interface configured for digital communication with one or more other computation devices and the validation computation is performed as a multi-party computation between the computation device and the one or more other computation devices.

7. A computation device as in claim 6, wherein at least one of the representations of one or more characters of the first string, the representations of one or more characters of the second string, the representation of the current position in the first string, the representation of the current position in the second string, and the representation of the edit script, is a secret-share of a secret-sharing between the computation device and the one or more other computation devices.

8. A computation device as in claim 6, wherein the first string is a private input to the multi-party computation of the computation device and the second string is a private input to the multi-party computation of one of the one or more other computation devices, orwherein the second string is a private input to the multi-party computation of the computation device and the first string is a private input to the multi-party computation of one of the one or more other computation devices.

9. A computation device as in claim 6, wherein the second string is a private input to the multi-party computation of the computation device or of one of the one or more other computation devices, the first string being a public input to the multi-party computation.

10. A computation device as in claim 1, wherein the computation device further comprises a communication interface configured for digital communication with a verification device, the validation computation being performed as a verifiable computation generating a cryptographic verifiable computation proof that the validation computation was performed successfully, the computation device being further configured to provide the cryptographic proof to the verification device.

11. A computation device as in claim 10, wherein the computation device is configured with a maximum edit distance between the first string and the second string, the set of allowed edit operations comprising dummy operations, the number of edit operations that the edit script comprises being a function of the length of the first string, the length of the second string, and the maximum edit distance.

12. A computation device as in claim 11, wherein the edit distance comprises the Levenshtein distance.

13. A computation device as in claim 12, wherein the processor is further configured to generate the edit script by identifying allowable edit operations from the first and second string and adding said identified allowable edit operation to the edit script, a dummy operation being added to the edit script if a mismatch or insertion operation is added to the edit script.

14. A computation device as in claim 13, wherein the first string and second string are nucleic acid sequences.

15. A verification device configured to verify that an edit script is for transforming a first string to a second string, the edit script comprising one or more edit operations, the edit operations being selected from a set of allowed edit operations, the set of allowed edit operations comprising match operations and difference operations, the verification device comprising:
- a communication interface configured for digital communication with a computation device,
- a processor configured to receive a proof from the computation device and verify the proof, the proof being a cryptographic verifiable computation proof that a validation computation was performed successfully, the validation computation comprising, for each edit operation in the edit script:
  - if the edit operation is a match operation, determining the character at the current position in the first string and the character at the current position in the second string, verifying that they match, incrementing the current position in the first string by one and incrementing the current position in the second string by one,
  - if the edit operation is a difference operation, incrementing the current position in the first string and/or the current position in the second string by one.

16. A verification device as in claim 15, wherein the proof is a cryptographic verifiable computation proof with respect to an input representation by a data providing device of the first string, of the larger string of which it is a substring, or of the root of the Merkle hash tree,
- the verification device being further configured to receive the input representation and verify that it has been authenticated by the data providing device, or
- the verification device being further configured to receive the input representation from the data providing device, the communication interface additionally being configured for digital communication with the data providing device.

17. A computation method for verifying that an edit script is for transforming a first string to a second string, the edit script comprising one or more edit operations, the edit operations being selected from a set of allowed edit operations, the set of allowed edit operations comprising match operations and difference operations, the computation method comprising:
- storing a representation of one or more characters of the first string, a representation of one or more characters of the second string, a representation of a current position in the first string, and a representation of a current position in the second string,
- obtaining a representation of the edit script, storing the representation in the memory, and subsequently performing a validation computation, the validation computation comprising, for each edit operation in the edit script:
  - if the edit operation is a match operation, determining the character at the current position in the first string and the character at the current position in the second string, verifying that they match, and incrementing the current position in the first string and the current position in the second string by one,
  - if the edit operation is a difference operation, incrementing the current position in the first string and/or the current position in the second string by one.

18. A non-transitory computer readable-medium comprising data representing instructions to cause a processor system to perform the method according to claim 17.

* * * * *